US011234991B2

(12) United States Patent
Harrington et al.

(10) Patent No.: US 11,234,991 B2
(45) Date of Patent: *Feb. 1, 2022

(54) METHODS FOR THE SEPARATION AND DETECTION OF AN OXYSTEROL

(71) Applicant: Warsaw Orthopedic, Inc., Warsaw, IN (US)

(72) Inventors: Roger E. Harrington, Collierville, TN (US); Jerbrena C. Jacobs, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 44 days.

This patent is subject to a terminal disclaimer.

(21) Appl. No.: 16/799,433

(22) Filed: Feb. 24, 2020

(65) Prior Publication Data

US 2020/0188415 A1 Jun. 18, 2020

Related U.S. Application Data

(60) Continuation of application No. 15/989,978, filed on May 25, 2018, now Pat. No. 10,596,182, which is a division of application No. 15/082,665, filed on Mar. 28, 2016, now Pat. No. 9,987,290.

(51) Int. Cl.
| | | |
|---|---|---|
| *C07C 41/00* | (2006.01) | |
| *A61K 31/00* | (2006.01) | |
| *G01N 33/74* | (2006.01) | |
| *A61K 31/575* | (2006.01) | |

(52) U.S. Cl.
CPC ......... *A61K 31/575* (2013.01); *G01N 33/743* (2013.01)

(58) Field of Classification Search
CPC ............................. C07C 41/00; A61K 31/575
See application file for complete search history.

(56) References Cited

U.S. PATENT DOCUMENTS

| 6,568,245 B2 | 5/2003 | Kaufman |
| 2014/0352411 A1 | 12/2014 | Yim et al. |
| 2015/0001018 A1 | 1/2015 | Kariyama et al. |
| 2015/0118277 A1 | 4/2015 | Parhami et al. |
| 2015/0140059 A1 | 5/2015 | Parhami et al. |
| 2015/0183726 A1 | 7/2015 | Singidi et al. |
| 2016/0159848 A1 | 6/2016 | Harrington et al. |

FOREIGN PATENT DOCUMENTS

WO 2009073186 A1 6/2009

OTHER PUBLICATIONS

Japan Patent Office, Notification of Reasons for Rejection, Japanese Patent Application No. 12018-551296, dated Aug. 24, 2020.
Montgomery Scott R et al., A Novel Oxysterol Compound for Therapeutic Development to Promote Bone Growth: Activation of Hedgehog Signaling and Osteogenesis through Smoothened Binding, 2014, Journal of Bone Mineral Research, vol. 29, No. 8, pp. 1872-1885, Supplementary Material.
Moreau Robert A., The Analysis of Lipids via HPLC with a Charged Aerosol Detector, 2006, Lipids, vol. 41, No. 7, pp. 727-734.
Hazotte A. et al., Comparison of universal detectors for high-temperature micro liquid chromatography, 2007, Journal of Chromatography A, vol. 1170, pp. 52-61.
Stappenbeck Frank et al., Novel oxysterols activate the Hedgehog pathway and induce osteogenesis, 2012, Bioorganic & Medicinal Chemistry Letters, vol. 22, pp. 5893-5897, Supplementary data.
Wall, Oliver, et al. Impurity profiling of carbocisteine by HPLC-CAD, qNMR and UV/vis spectroscopy. Journal of Pharmaceutical and Biomedical Analysis. Vol. 95 (2014) pp. 1-10.
Liu ke et al., Determination of tenuifolin in Radix polygalae by HPLC-CAD. Journal of Northwest Pharmacy, Jan. 10, 2016. Abstract in English.
Li Qin et al. Determination of related substances in Palmitic acid by HPLC-CAD. China Medicine and Pharmacy, Mar. 15, 2015. Abstract in English.
Second Chinese Office Action issued by the China State IP Office in corresponding Chinese Patent Application No. CN201780019899.3. dated May 10, 2021. English translation.
European Patent Office, Application No. 1 7 776 387.7, Examination Report—Communication pursuant to Article 94 (3) EPC, dated Jun. 29, 2020.
Extended European Search Report, dated Oct. 8, 2019, issued by the European Patent Office in EP Appl. No. 17776387.7 for Methods for the Separation and Detection of an Oxysterol, filed on Mar. 27, 2017.
Montgomery, Scott, et al. "A Novel Osteogenic Oxysterol Compound for Therapeutic Development to Promote Bone Growth: Activation of Hedgehog Signaling and Osteogenesis Through Smoothened Binding," Journal of Bone and Mineral Research, vol. 29, No. 8, Jul. 21, 2014, pp. 1872-1885.
Narayanaswamy, Rohini, et al. "Simultaneous Determination of Oxysterols, Cholesterol and 25-Hydroxy-Vitamin D3 in Human Plasma by LC-UV-MS," PLOS One, vol. 10, No. 4, Apr. 13, 2015, p. e0123771.
Sugimoto, Hiroshi, et al. "Method development for the determination of 24S-hydroxycholesterol in human plasma without derivatization by high-performance liquid chromatography with tandem mass spectrometry in atmospheric pressure chemical ionization mode: Liquid Chromatography," Journal of Separation Science, vol. 38, No. 20, Sep. 10, 2015, pp. 3516-3524.

(Continued)

*Primary Examiner* — Sikarl A Witherspoon
(74) *Attorney, Agent, or Firm* — Sorell, Lenna & Schmidt, LLP; William D. Schmidt, Esq.

(57) ABSTRACT

Assay methods for determining purity of a sample of a sterol are provided. These methods include providing an HPLC eluent including a sterol, other compounds related to the sterol and a mobile volatile phase; generating an aerosol of liquid droplets from the HPLC eluent; drying the liquid droplets to obtain residue particles of the sterol; contacting the residue particles of the sterol with an ion stream which applies a size-dependent electrical charge to each of the residue particles to generate an electrical signal and measuring the electrical signal to determine the purity of the sterol in the sample. The sterol can be OXY133 or OXY133 monohydrate.

19 Claims, 12 Drawing Sheets

(56) References Cited

OTHER PUBLICATIONS

Brouwers, Jos F., et al. "Mass Spectrometric Detection of Cholesterol Oxidation in Bovine Sperm," Biology of Reproduction, vol. 85, No. 1, Jul. 1, 2011, pp. 128-136.

Burkard, Ines, et al. "Determination of 24S- and 27-hydroxycholesterol in plasma by high-performance liquid chromatography-mass spectrometry," Journal of Lipid Research, vol. 45, No. 4, Apr. 1, 2004, pp. 776-781.

Mutemberezi, Valentin, et al. "Development and validation of an HPLC-MS method for the simultaneous quantification of key oxysterols, endocannabidoids, and ceramides: variations in metabolic syndrome," Analytical and Bioanalytical Chemistry, Springer, DE, vol. 408, No. 3, Nov. 12, 2015, pp. 733-745.

Hazotte, et al. "Comparison of universal detectors for high-temperature micro liquid chromatography," Journal of Chromatography A, Elsevier, Amsterdam, NL, vol. 1170, No. 1-2, Oct. 11, 2007, pp. 52-61.

Kielbowicz, Grzegorz, et al. "Separation and Quantification of Phospholipid and Neutral Lipid Classes by HPLC-CAD Application to Egg Yolk Lipids," Journal of Liquid Chromatography and Related Technologies, vol. 38, No. 8, Feb. 19, 2015, pp. 898-903.

Moreau, Robert A. "The analysis of lipids via HPLC with a charged aerosol detector," LIPIDS, vol. 41, No. 7, Jul. 1, 2006, pp. 727-734.

Scott R Montgomery et al: "A Novel Osteogenic Oxysterol Compound for Therapeutic Development to Promote Bone Growth: Activation of Hedgehog Signaling and Osteogenesis Through Smoothened Binding", Journal of Bone and Mineral Research, vol. 29, No. 8, Jul. 21, 2014 (Jul. 21, 2014), pp. 1872-1885.

Rohini Narayanaswamy et al: "Simultaneous Determination of Oxysterols, Cholesterol and 25-Hydroxy-Vitamin 03 in Human Plasma by LC-UV-MS", PLOS One, vol. 10, No. 4, Apr. 13, 2015 (Apr. 13, 2015), p. e0123771.

Hiroshi Sugimoto et al: "Method development for the determination of 24S-hydroxycholesterol in human plasma without derivatization by high-performance liquid chromatography with tandem mass spectrometry in atmospheric pressure chemical ionization mode : Liquid Chromatography", Journal of Separation Science., vol. 38, No. 20, Sep. 10, 2015 (Sep. 10, 2015), pp. 3516-3524.

Jos F. Brouwers et al: "Mass Spectrometric Detection of Cholesterol Oxidation in Bovine Sperm", Biology of Reproduction, vol. 85, No. 1, Jul. 1, 2011 (Jul. 1, 2011), pp. 128-136.

Ines Burkard et al: "Determination of 24S- and 27-hydroxycholesterol in plasma by high-performance liquid chromatography-mass spectrometry", Journal of Lipid Research, vol. 45, No. 4, Apr. 1, 2004 (Apr. 1, 2004), pp. 776-781.

Mutemberezi Valentin et al: "Development and validation of an HPLC-MS method for the simultaneous quantification of key oxysterols, endocannabinoids, and ceramides: variations in metabolic syndrome", Analytical and Bioanalytical Chemistry, Springer, DE, vol. 408, No. 3, Nov. 12, 2015 (Nov. 12, 2015), pp. 733-745.

Hazotte et al: "Comparison of universal detectors for high-temperature micro liquid chromatography", Journal of Chromatography A, Elsevier, Amsterdam, NL, vol. 1170, No. 1-2, Oct. 11, 2007 (Oct. 11, 2007), pp. 52-61.

Grzegorz Kielbowicz et al: "Separation and Quantification of Phospholipid and Neutral Lipid Classes by HPLC-CAD: Application to Egg Yolk Lipids", Journal of Liquid Chromatography and Related Technologies, vol. 38, No. 8, Feb. 19, 2015 (Feb. 19, 2015), pp. 898-903.

Robert A. Moreau: "The analysis of lipids via HPLC with a charged aerosol detector", LIPIDS, vol. 41, No. 7, Jul. 1, 2006 (Jul. 1, 2006), pp. 727-734.

Extended European Search Report issued by the European Patent Office, dated Apr. 29, 2021, in corresponding European patent application No. 21153543.0.

Scott R Montgomery et al, "A Novel Osteogenic Oxysterol Compound for Therapeutic Development to Promote Bone Growth: Activation of Hedgehog Signaling and Osteogenesis Through Smoothened Binding", Journal of Bone and Mineral Research, US, (Jul. 21, 2014), vol. 29, No. 8, p. 1872.

Rohini Narayanaswamy et al., "Simultaneous Determination of Oxysterols, Cholesterol and 25-Hydroxy-Vitamin D3 in Human Plasma by LC-UV-MS", PLOS One, (Apr. 13, 2015), vol. 10, No. 4, p. E0123771.

Hiroshi Sugimoto et al, "Method development for the determination of 24S-hydroxycholesterol in human plasma without derivatization by high-performance liquid chromatography with tandem mass spectrometry in atmospheric pressure chemical ionization mode : Liquid Chromatography", Journal of Separation Science., DE, (Sep. 10, 2015), vol. 38, No. 20, p. 3516-3524.

Jos F. Brouwers et al, "Mass Spectrometric Detection of Cholesterol Oxidation in Bovine Sperm", Biology of Reproduction, US, (Nov. 17, 2011), vol. 85, No. 1, doi:10.1095/biolreprod.111.091207, ISSN 0006-3363, p. 128-136.

Ines Burkard et al., "Determination of 24S- and 27-hydroxycholesterol in plasma by high-performance liquid chromatography-mass spectrometry", Journal of Lipid Research, US, (Jan. 16, 2004), vol. 45, No. 4, p. 776-781.

Mutemberezi Valentin et al, "Development and validation of an HPLC-MS method for the simultaneous quantification of key oxysterols, endocannabinoids, and ceramides: variations in metabolic syndrome", Analytical and Bioanalytical Chemistry, Springer, DE, vol. 408, No. 3, pp. 733-745, (Nov. 12, 2015).

Hazotte et al, "Comparison of universal detectors for high-temperature micro liquid chromatography", Journal of Chromatography A, Elsevier, Amsterdam, NL, (Oct. 11, 2007), vol. 1170, No. 1-2, p. 52-61.

Grzegorz Kielbowicz et al., "Separation and Quantification of Phospholipid and Neutral Lipid Classes by HPLC-CAD: Application to Egg Yolk Lipids", Journal of Liquid Chromatography and Related Technologies, (Feb. 19, 2015), vol. 38, No. 8, p. 898-903.

Robert A. Moreau, "The analysis of lipids via HPLC with a charged aerosol detector", Lipids, DE, (Jul. 1, 2006), vol. 41, No. 7, p. 727-734.

Stappenbeck et al: Novel oxysterols activate the Hedgehog pathway and induce osteogenesis. Biorganic & Medicinal Chemistry Letters 22(18), p. 2893-5897, 2012. https://www.sciencedirect.com/science/article/abs/pii/S0960894X12009584.

Acworth et al: Simple and direct analysis of red palm oil by reversed phase HPLC and charged aerosol detection. Planta Medica 77, 2011.** https://www.thieme-connect.com/products/ejournals/abstract/10.1055/s-0031-1282198. Abstract.

Relatório De Busca (Office Action) dated Jun. 24, 2021 issued by Serviço Público Federal Ministério Da Economia Instituto Nacional Da Propriedade Industrial (Brazilian Patent Office) in corresponding Brazilian Patent Application No. BR112018069654-4 filed Mar. 27, 2017.

Written Opinion of the Federal Public Service Ministry of Economy National Institute of Industrial Property (Brazilian Patent Office) in corresponding Brazilian Patent Application No. BR112018069654-4 filed Mar. 27, 2017.

International Search Report and Written Opinion for PCT/US2017/024295 the counterpart application dated Jun. 16, 2017, 10 pages.

Acworth, et al.—Simple and Direct Analysis of Phytosterols in Red Palm Oil by Reversed-Phase HPLC and Charged Aerosol Detection, Thermo Fisher Scientific, Chelmsford, MA, USA, 2011, www.thermoscientific.com/dionex, 5 pages.

Almeling, et al.—Charged aerosol detection in pharmaceutical analysis, Journal of Pharmceutical and Biomedical Analysis, 69 (2012) 50-63, Elsevier, www.elsevier.com/locate/jpba, 14 pages.

Awad, et al.—Charged Aerosol Detection in Pharmaceutical Analysis an Overview LCGC, Explore the Science of Cannabis, The 2016 Emerald Conference, Apr. 1, 2009, 3 pages.

Reviewer Guidance—Validation of Chromatographic Methods by Center for Drug Evaluation and Research (CDER), Nov. 1994, 33 pages.

Dixon—Development and Testing of a Detection Method for Liquid Chromatography Based on Aerosol Charging, Chemistry Depart-

(56) References Cited

OTHER PUBLICATIONS ment, California State University, 600 J Street, Sacramento, CA 95819-6057, Anal. Chem., Jul. 1, 2002, vol. 74, No. 13, 2930-2937, 8 pages.
Fireman, Quantitative HPLC Analysis of Lipids, Mon, Jan. 9, 2006, 9:46 am, Bioscience Technology, 6 pages.
Gorecki, et al.—Universal Response in Liquid Chromatography Using Charged Aerosol Detection, Anal. Chem., May 1, 2006, vol. 78, No. 9, 3186-3192, 7 pages.
Holzgrabe, et al.—Identification and control of impurities in streptomycin sulfate by high performance liquid chromatography coupled with mass detection and corona charged aerosol-detection, Journal of Pharmceutical and Biomedical Analysis, 56 (2011) 271-279, Elsevier, www.elsevier.com/locate/jpba, 9 pages.
Ganan, et al.—ICH Q5C, Stability Testing of Biotechnological / Biological products, ICGH CGC ASEAN Training, Kuala Lumpur, May 30-31, 2011, European Medicines Agency, Science Medicines Health, Human Medicines Development and Evaluation, 81 pages.
Moreau, The Analysis of Lipids via HPLC with a Charged Aerosol Detector, U.S. Dept. of Agriculture, Agricultural Research Service, Eastern Regional Research Center, Wyndmoore, PA, Lipids, vol. 41, No. 7, 2006, 8 pages.
Moreau, Lipid analysis via HPLC with a charged aerosol detector*, Lipid Technology, Aug./Sep. 2009, vol. 21, No. 8/9, WILEY-VCH Verlag GmbH & Co. KGaA, Weinheim, www.lipid-technology.com, 4 pages.
Levin, Quantitative Work in HPLC, Medtechnica, www.forumsci.co.il/HPLC, Shula_Levin@medtechnica.co il, 97 pages.
Sinclair, et al.—Charged Aerosol Detection. Factors for consideration in its use as a generic quantitative detector, Global Compound Sciences/DMPK, AstraZeneca, Mereside, Alderley Park, Macclesfield, Cheshire, SK10 4TG, Chromatography Today, vol. 1, Issue 3, Jun. 2008, 7 pages.
Stypulkowska, et al.—Determination of Gentamicin Sulphate Composition and Related Substances in Pharmaceutical Preparations by LC with Charged Aerosol Detection, Chromotographia, Dec. 2010, 72, No. 11/12, 1225-1229, 5 pages.
Swartz, et al.—An Overview of Corona Charged Aerosol Detection in Pharmaceutical Analysis, White Paper, SMITHERS Synomics Pharma, Synomics Pharmaceutical Services, LLC, 790 Main Street, Wareham, MA 02571-1037, www.synomicspharma.com, 12 pages.
Teutenberg, et al.—Evaluation of column bleed by using an ultraviolet and a charged aerosol detector coupled to a high-temperature liquid chromatographic system, Journal of Chromatography A, 2006, 197-201, www.sciencedirect.com, Elsevier, www.elsevier.com/locate/chroma, 5 pages.
Thermo Scientific, Your hidden peaks revealed with clearer vision using charged aerosol detection technology, www.thermoscientific.com/en/about-us/promotions/thermo-scientific-dionex-corona-veo-charged-aerosol-detector-html. 6 pages.
Vehovec, et al.—Review of operating principle and applications of the charged aerosol detector, Journal of Chromatography A, 1217, 2010, 1549-1556, Elsevier, www.elsevier.com/locate/chroma, 8 pages.
Vervoot, et al. - Performance evaluation of evaporative light scattering detection and charged aerosol detection in Yeversed phase liquid chromatography, www.sciencedirect.com, Journal of Chromatography A, 1189, 2008, 92-100, ELSEVIER, www.elsevier.com/locate/chroma, 9 pages.

METHODS FOR THE SEPARATION AND DETECTION OF AN OXYSTEROL

BACKGROUND

Different biological substances are commonly employed to promote bone growth in medical applications including fracture healing and surgical management of bone disorders including spinal disorders. Spine fusion is often performed by orthopedic surgeons and neurosurgeons alike to address degenerative disc disease and arthritis affecting the lumbar and cervical spine. Historically, autogenous bone grafting, commonly taken from the iliac crest of the patient, has been used to augment fusion between vertebral levels.

One protein that is osteogenic and commonly used to promote spine fusion is recombinant human bone morphogenetic protein-2 (rhBMP-2). Its use has been approved by the US Food and Drug Administration (FDA) for single-level anterior lumbar interbody fusion. The use of rhBMP-2 has increased significantly since this time and indications for its use have expanded to include posterior lumbar spinal fusion as well as cervical spine fusion.

Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is Oxy133 or (3S,5S,6S,8R,9S,10R, 13S, 14S,17S) 17-((S)-2-hydroxyoctan-2-yl)-10,13-dimethylhexadecahydro-1H-cyclopenta[a]phenanthrene-3,6-diol, which exhibits the following structures:

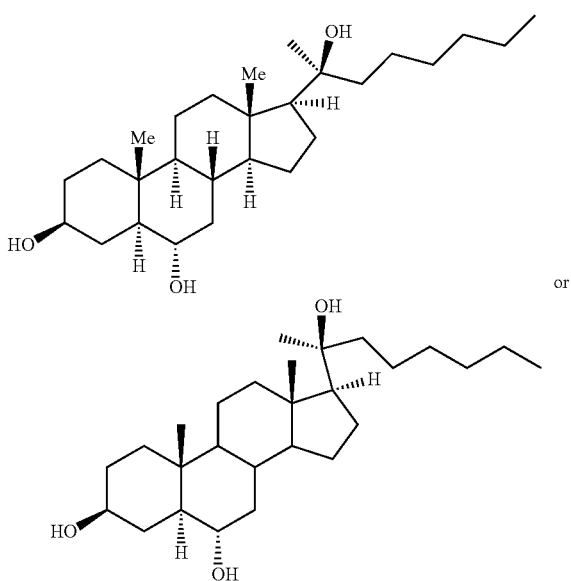

Oxy133 is a synthetic small molecule that promotes bone growth in mammals. Currently, the oxysterol class of compounds is analyzed using gas chromatography (GC) with derivatization. This is a lengthy process that requires heating of the samples and is not preferred by regulatory agencies. Currently available industry detection techniques paired with high performance liquid chromatography (HPLC) are not robust or sensitive enough to detect Oxy133 in the presence of related impurities and degradation.

The Oxy133 molecule lacks a chromophore making chromatography insufficient. In addition, known impurities closely related to the parent compound are difficult to detect by techniques such as evaporative light scattering (ELS), refractive index (RI), and mass spectrometry (MS).

Evaluation of purity is required to assure the safety and efficacy of OXY133 and is often achieved by applying an HPLC/UV method. Standard industry detection techniques paired with HPLC are not robust or sensitive enough to detect OXY133 in the presence of related impurities and degradation.

When OXY133 is in a monohydrate form, there is often difficulty analyzing Oxy133 monohydrate due to the presence of related impurities, for example, diastereomers, which need to be separated, quantified and identified. Known impurities are closely related to the parent compound and are difficult to detect by techniques such as evaporative light scattering (ELS), refractive index (RI), and mass spectrometry (MS.)

Therefore, a need to overcome the drawbacks of these detection techniques and to provide reliable analytical methods for the determination of content and purity in samples containing an OXY133 product as part of critical-path activities during the analytical method development (AMD) phase required to validate ICH quality control guidelines. Methods to determine purity in a sample of OXY133 which do not rely on presence of chromophores in the sample would be beneficial. Methods which can detect non-volatile analytes or residues would also be beneficial.

SUMMARY

In some embodiments, an assay method for determining purity of a sample of OXY133 is provided, the method comprising providing an HPLC eluent including OXY133, OXY133 impurities and a mobile volatile phase; generating an aerosol of liquid droplets from the HPLC eluent; drying the droplets to obtain residue particles of OXY133; contacting the OXY133 residue particles with an ion stream which applies a size-dependent electrical charge to each of the residue particles to generate an electrical signal having a level proportional to the amount of charged residue particles of OXY133; and measuring the electrical signal to determine the purity of OXY133 in the sample. In several embodiments, OXY133 comprises OXY133 monohydrate.

In various aspects, the assay method of the present disclosure can be used to separate OXY133 monohydrate from diastereomer D1, diastereomer D2 or other OXY133 monohydrate impurities, for example $C_{27}H_{46}O_2$ diol, which is used to synthesize OXY133 monohydrate. In various embodiments, the assay method of this disclosure can detect OXY133 monohydrate impurities from about 0.03% to about 0.05% w/w or w/v based on the total weight of the composition. The resolution of the OXY133 peak and the D1 diastereomer that can be achieved using the assay method of this disclosure can be ≥0.8. In many embodiments, the limit of detection of the OXY133 monohydrate is about 0.01% or 1 ng. Further, the purity of OXY133 monohydrate that can be achieved by using the assay method of this disclosure is at least 96.9%.

In various other embodiments, a method is provided for separating OXY133 monohydrate from a sample, the method comprising providing an OXY133 monohydrate reference standard; providing the sample having a concentration equivalent to OXY133 monohydrate reference standard; determining the amount of OXY133 monohydrate in the reference standard by HPLC-CAD; determining the amount of OXY133 monohydrate in the sample by HPLC-CAD; and comparing the amount of OXY133 monohydrate in the sample to the amount of OXY133 monohydrate in the reference standard. In some embodiments, in the method of this disclosure the reference standard concentration is present in an amount of at least 500 µg/mL. In other aspects, the sample is prepared in a solution of acetonitrile: tetrahydrofuran, 1:1, volume by volume. In yet other aspects, the sample comprises a mobile phase from the HPLC-CAD, which is 100% water or 100% methanol.

In some embodiments a method for determining purity in a sample of a sterol is provided, the method comprising: preparing sterol by reacting an organometallic compound with pregnenolone or pregnenolone acetate to form the sterol, the sterol having the formula:

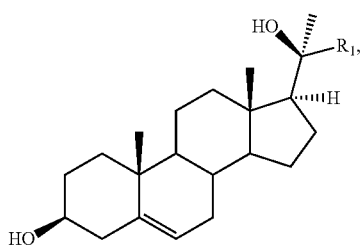

or a pharmaceutically acceptable salt, hydrate or solvate thereof, wherein $R_1$ comprises an aliphatic or cyclic substituent having at least one carbon atom; subjecting the sterol to HPLC to obtain an eluent comprising the sterol, impurities of the sterol and a volatile mobile phase; charging the HPLC eluent into a CAD detector to determine the purity of the sterol. In various embodiments, the sterol is OXY133 and in other embodiments the sterol is OXY133 monohydrate.

In some embodiments, a method for determining purity in a sample of a oxysterol is provided, the method comprising: preparing a sterol by reacting a diol having the formula:

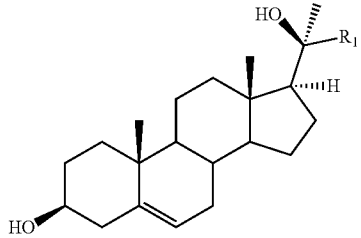

with borane and hydrogen peroxide to form the oxysterol or a pharmaceutically acceptable salt, hydrate or solvate thereof having the formula:

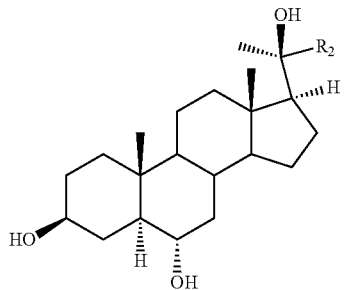

wherein $R_1$ comprises an aliphatic or cyclic substituent having at least one carbon atom, and wherein $R_2$ comprises an aliphatic or cyclic substituent having at least one carbon atom; subjecting the oxysterol to HPLC to obtain an eluent comprising the oxysterol, impurities of the oxysterol and a volatile mobile phase; charging the HPLC eluent into a CAD detector to determine the purity of the oxysterol. In various embodiments, the oxysterol is OXY133 monohydrate.

In some embodiments, a method for determining purity in a sample of an oxysterol is provided, the method comprising preparing an oxysterol by reacting a diol having the formula:

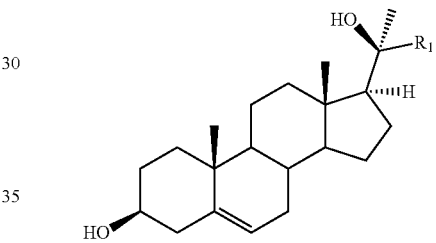

with a borane compound to form the oxysterol or a pharmaceutically acceptable salt, hydrate or solvate thereof having the formula:

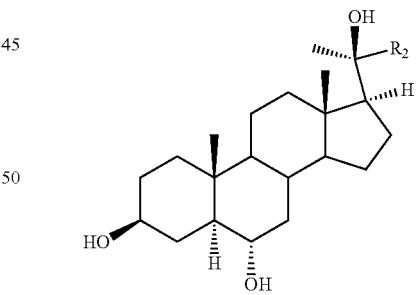

wherein $R_1$ comprises an aliphatic or cyclic substituent having at least one carbon atom, and $R_2$ comprises an aliphatic or cyclic substituent having at least one carbon atom; subjecting the oxysterol to HPLC to obtain an eluent comprising the oxysterol, impurities of the oxysterol and a volatile mobile phase; charging the HPLC eluent into a CAD detector to determine the purity of the oxysterol. In various embodiments, the oxysterol is OXY133 monohydrate.

In some embodiments, a method for determining purity in a sample of an oxysterol is provided, the method comprising reacting a diol having the formula:

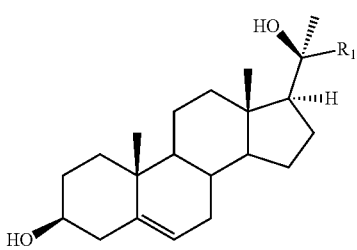

with borane, hydrogen peroxide and tetrahydrofuran to form the oxysterol or a pharmaceutically acceptable salt, hydrate or solvate thereof having the formula:

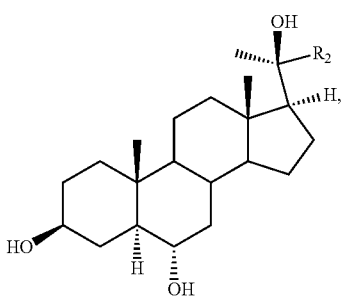

wherein $R_1$ comprises an aliphatic or cyclic substituent having at least one carbon atom, and $R_2$ comprises an aliphatic or cyclic substituent having at least one carbon atom; subjecting the oxysterol to HPLC to obtain an eluent comprising the oxysterol, impurities of the oxysterol and a volatile mobile phase; charging the HPLC eluent into a CAD detector to determine the purity of the oxysterol. In various embodiments, the oxysterol is OXY133 monohydrate.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
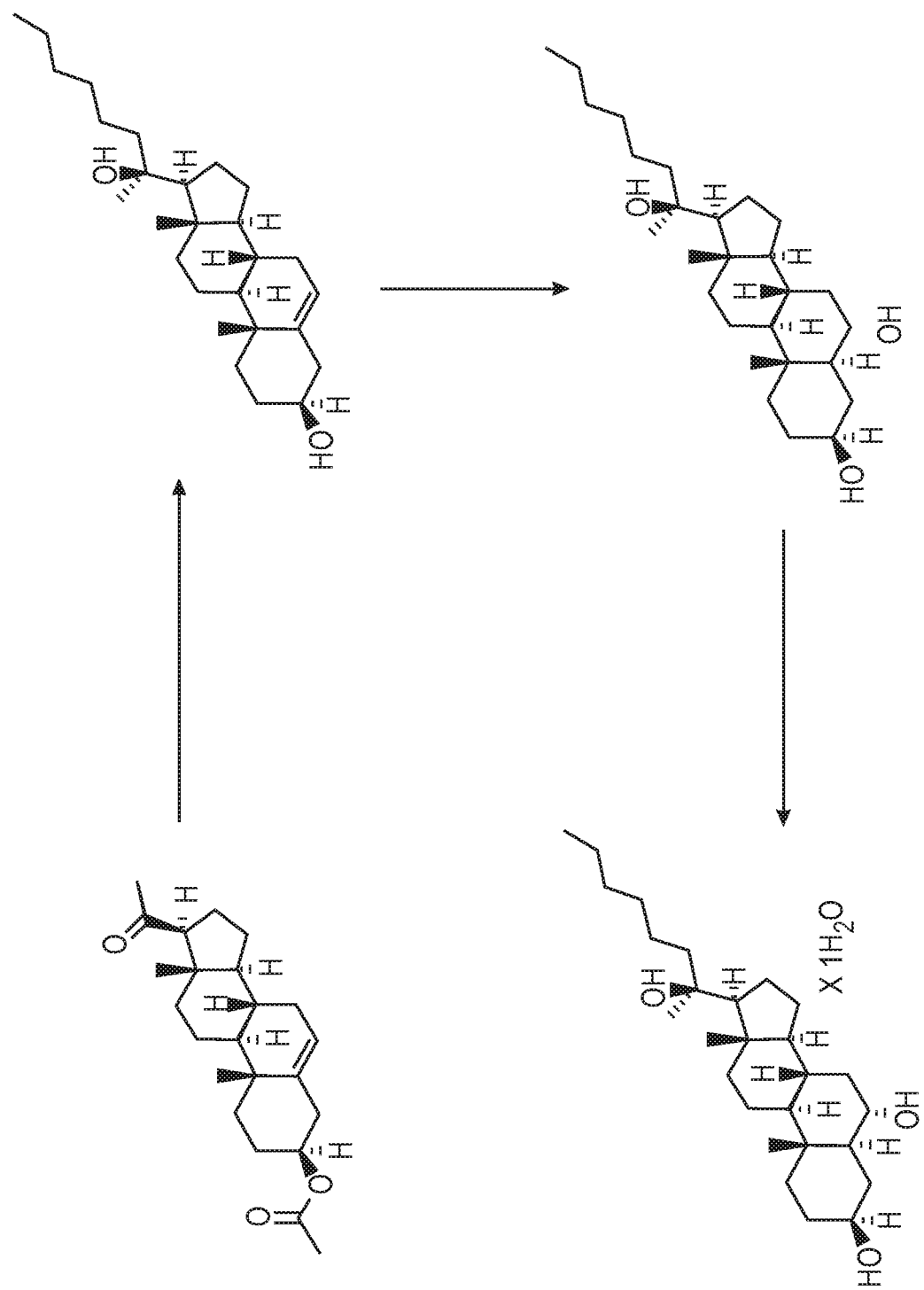
FIG. 1 illustrates a step-wise reaction for synthesizing Oxy133 with starting reactants comprising pregnenolone acetate, as shown in one embodiment of this disclosure. The pregnenolone is reacted with an organometallic compound to produce a sterol or diol having two hydroxyl groups. The sterol or diol is then reacted with borane and hydrogen peroxide and purified to produce Oxy133.
Figure 2:
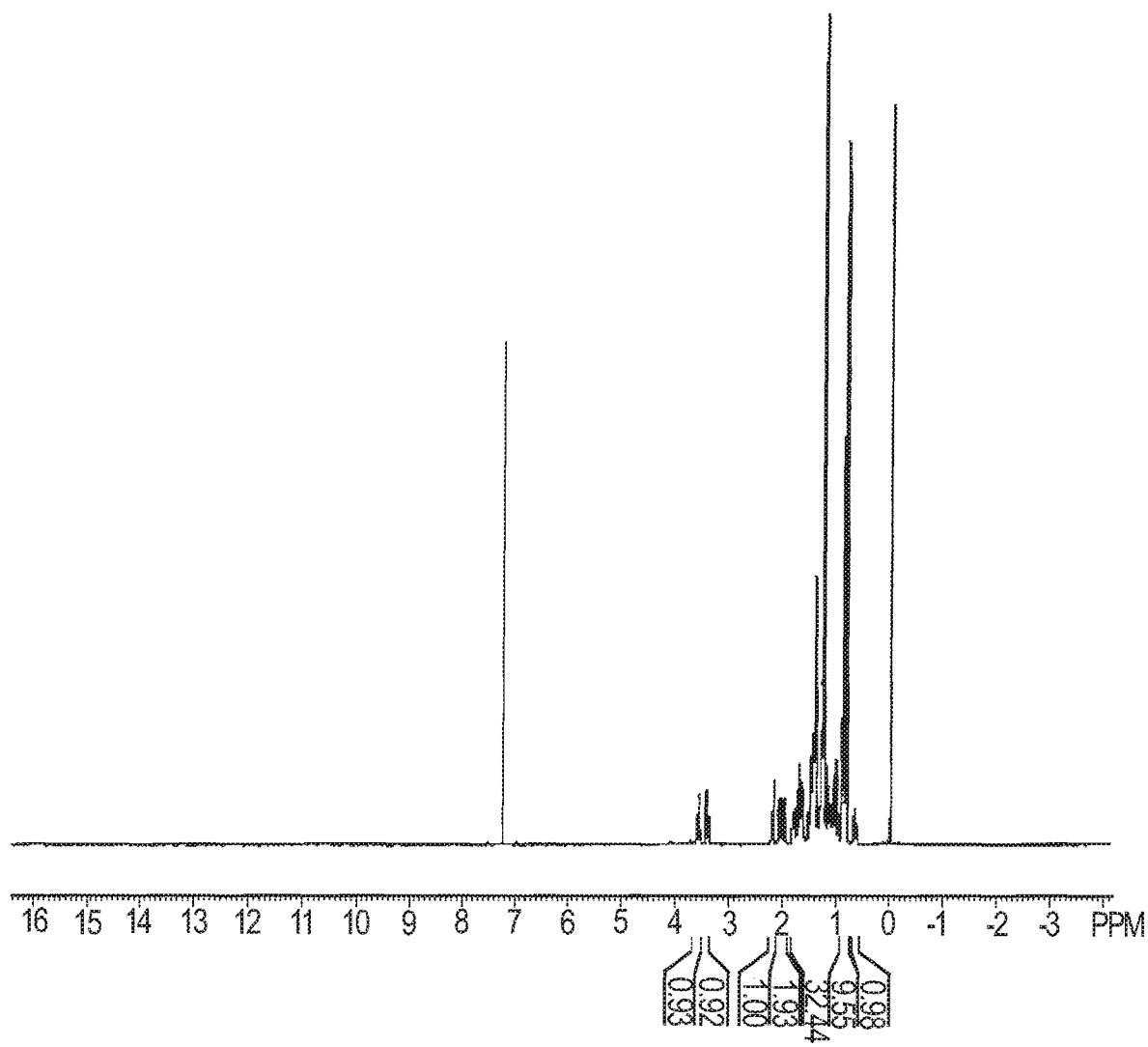
FIG. 2 is a graphic illustration of the $^1$H NMR data obtained from isolated and purified Oxy133.
Figure 3:
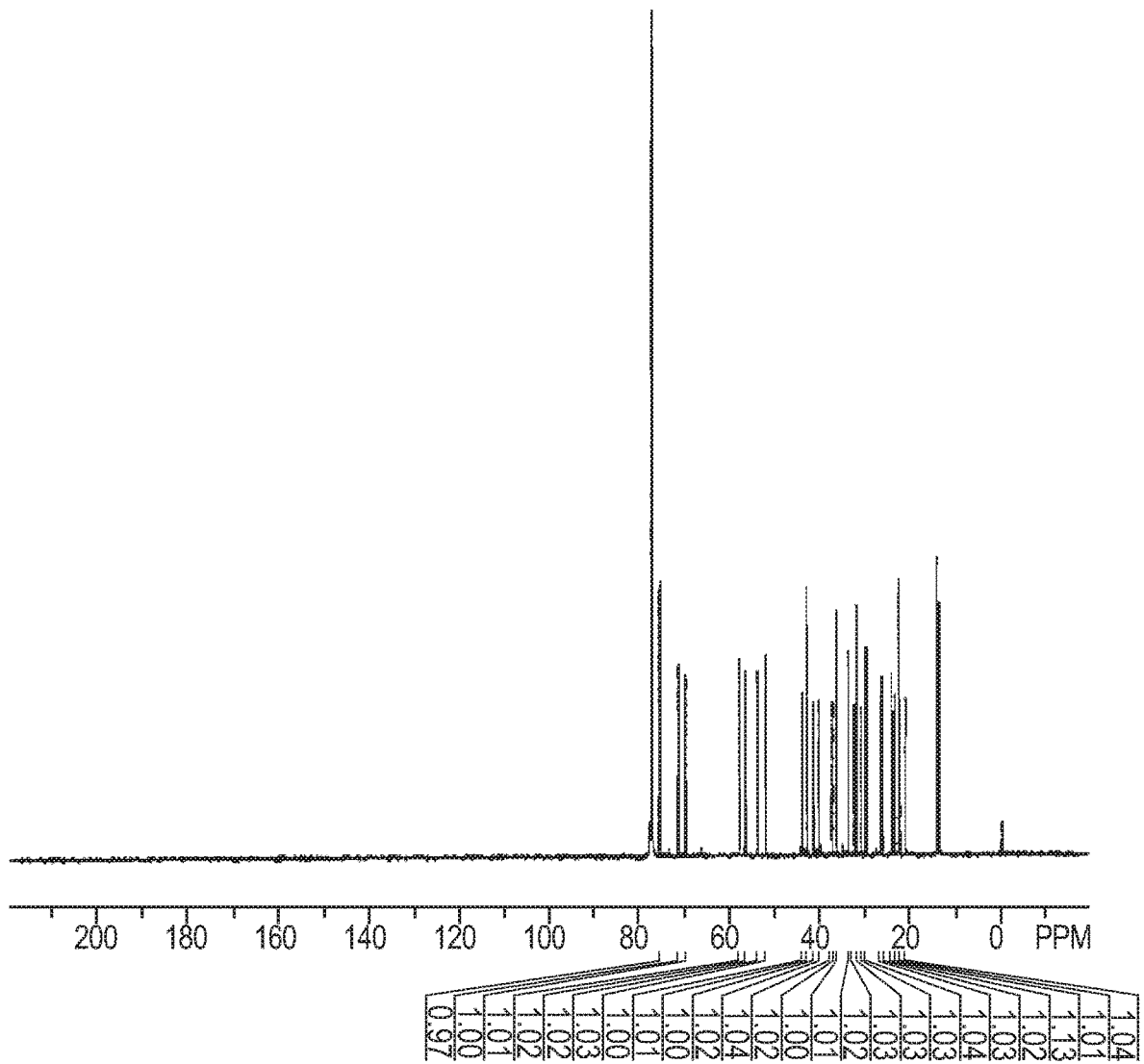
FIG. 3 is a graphic illustration of the $^{13}$C NMR data obtained from Oxy133.
Figure 4:
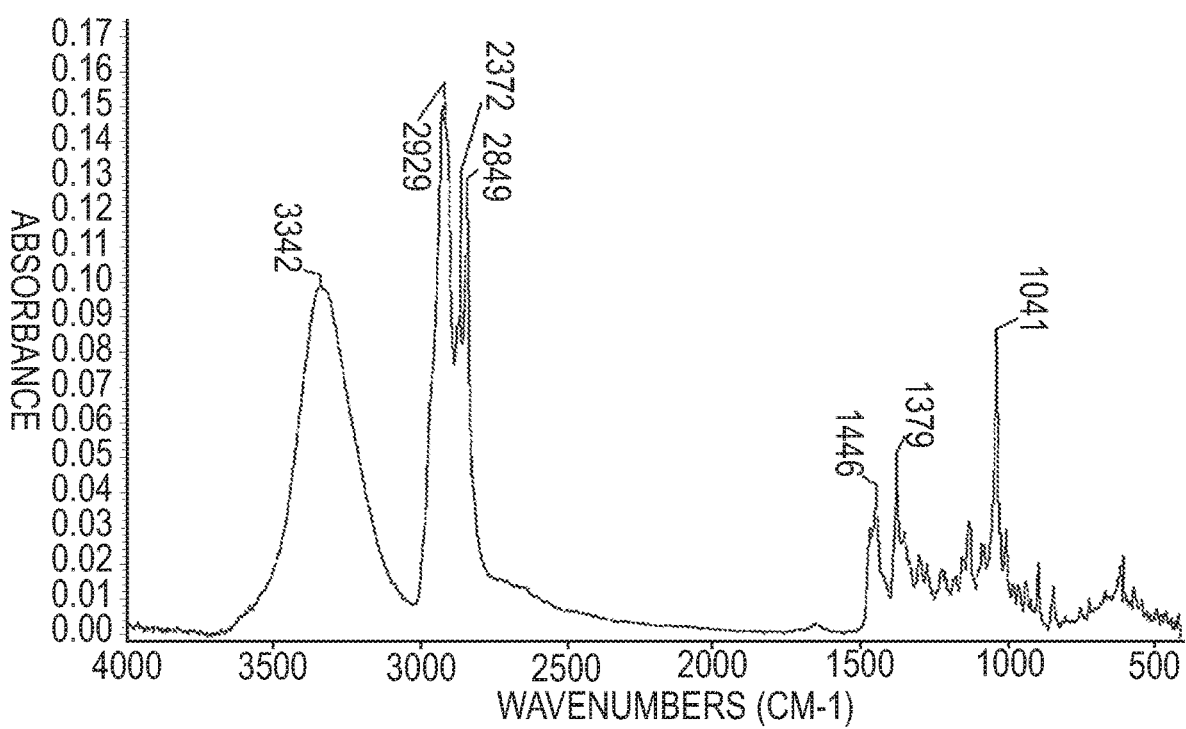
FIG. 4 is a graphic illustration of the infrared spectroscopy data obtained from Oxy133.
Figure 5:
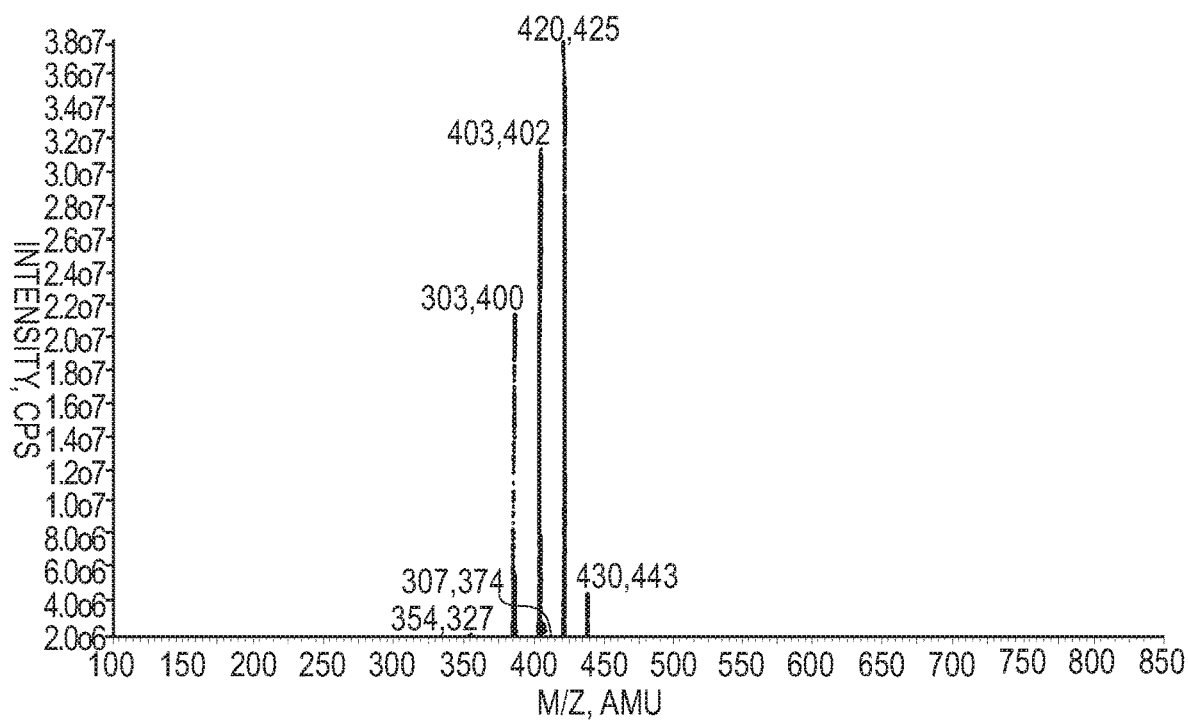
FIG. 5 is a graphic illustration of the mass spectroscopy data obtained from Oxy133.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug". It will be understood that unless otherwise specified a "drug" formulation may include more than one therapeutic agent, wherein exemplary combinations of therapeutic agents include a combination of two or more drugs. The term "drug" is also meant to refer to the "API" whether it is in a crude mixture or purified or isolated.

The term "biodegradable" includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "bioerodible" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" and/or "alkynyl" is used, as defined below. In some embodiments, the alkyl groups are (C1-C40) alkyl. In some embodiments, the alkyl groups are (C1-C6) alkyl.

The term "alkanyl" as used herein refers to a saturated branched, straight-chain or cyclic alkyl radical derived by the removal of one hydrogen atom from a single carbon atom of a parent alkane. Typical alkanyl groups include, but are not limited to, methanyl; ethenyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are (C1-C40) alkanyl. In some embodiments, the alkanyl groups are (C1-C6) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkynyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl (ethano); propan-1,3-diyl(propano); butan-1,4-diyl(butano); and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkanyl," "heteroalkyldiyl" and "heteroalkyleno" as used herein refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, O—O—, —S—S—, —O—S—, —NR', =N—N=, —N=N—, —N(O)N—, —N=N—NR'—, —PH—, —P(O)2-, —O—P(O)2-, —SH2-, —S(O)2-, or the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

The term "aryl" as used herein refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. Some preferred aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some preferred aryldiyl groups are divalent radicals derived from benzene and naphthalene, especially phena-1,4-diyl, naphtha-2,6-diyl and naphtha-2,7-diyl.

The term "arydeno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

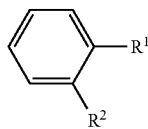

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphthaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc. Thus, in the above example, when $R^1$ taken together with $R^2$ is [2,3]naphthaleno, the resultant compound is anthracene. When $R^1$ taken together with $R^2$ is [1,2]naphthaleno, the resultant compound is phenanthrene. In a preferred embodiment, the aryleno group is (C5-C14), with (C5-C10) being even more preferred.

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-C14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a (C1-C10) aromatic. Some preferred are arylaryl groups in which all of the parent aromatic ring systems are identical, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. One preferred biaryl group is biphenyl.

The term "arylalkyl" as used herein refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some preferred embodiments the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl, with 5-10 membered heteroaryl being particularly preferred. Some preferred heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. Some preferred heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

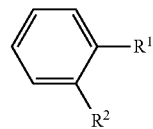

wherein $R^1$, when taken alone is hydrogen, or when taken together with $R^1$ is 5-14 membered heteroaryleno; and $R^2$, when taken alone is hydrogen, or when taken together with $R^1$ is 5-14 membered heteroaryleno;

When $R^1$ and $R^2$ are each hydrogen, the resultant compound is benzene. When $R^1$ taken together with $R^2$ is a 6-membered heteroaryleno pyridino), the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2] pyridino, [2,3]pyridino, [3,4]pyridino, etc. Thus, in the above example, when $R^1$ taken together with $R^2$ is [1,2] pyridino, the resultant compound is quinolizine. When $R^1$ taken together with R2 is [2,3]pyridino, the resultant compound is quinoline. When $R^1$ taken together with $R^2$ is [3,4]pyridino, the resultant compound is isoquinoline. In preferred embodiments, the heteroaryleno group is 5-14 membered heteroaryleno or 5-10 membered heteroaryleno. Some preferred heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyndmo, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridyl-purinyl, bipurinyl, etc. When the number of ring atoms are specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, more preferably a 5-10 membered heteroaromatic. Also preferred are heteroaryl-heteroaryl groups in which all of the parent heteroaromatic ring systems are identical. Some preferred heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. Some preferred biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In some preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, perhalo (C1-C6) alkyl, —CX3, —CF3, —CN, —OCN, —SCN, —NCO, —NCS, —NO, —NO2, =N2, —N3, —S(O)2O—, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol, sterol or diol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol, sterol or diol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol, sterol, or diol to assist in obtaining a controlled release depot effect, the oxysterol, sterol, or diol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The term "solvate" is a complex or aggregate formed by one or more molecules of a solute, e.g. a compound or a pharmaceutically-acceptable salt thereof, and one or more molecules of a solvent. Such solvates can be crystalline solids having a substantially fixed molar ratio of solute and solvent. Suitable solvents include for example, water, ethanol, etc.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure. Sometimes the phrase "administration of Oxy133" is used herein in the context of administration of this compound to a subject (e.g., contacting the subject with the compound, injecting the compound, administering the compound in a drug depot, etc.). It is to be understood that the compound for such a use can generally be in the form of a pharmaceutical composition or bioactive composition comprising the Oxy133.

The term "an OXY133 product" includes OXY133, OXY133 monohydrate, as well as its diastereomers, D1 and D2.

The term "impurity" is used herein to refer to an impurity of OXY133 or OXY133 monohydrate including diastereomer D1, diastereomer D2 or other OXY133 monohydrate impurity, for example $C_{27}H_{46}O_2$ diol used to synthesize OXY133 monohydrate or any combinations thereof.

A "therapeutically effective amount" or "effective amount" is such that when administered, the oxysterol (e.g., Oxy133), sterol, diol, results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, 99.9% or 99.999% less than the oral dosage or injectable dose.

The term "mammal" refers to organisms from the taxonomy class "mammalian," including but not limited to humans, other primates such as chimpanzees, apes, orangutans and monkeys, rats, mice, cats, dogs, cows, horses, etc.

The oxysterol can be "osteogenic," where it can enhance or accelerate the ingrowth of new bone tissue by one or more mechanisms such as osteogenesis, osteoconduction and/or osteoinduction.

New compositions and methods are provided to efficiently and safely make oxysterols including Oxy133. Methods and compositions that can efficiently and safely generate Oxy133 are also provided.

The section headings below should not be restricted and can be interchanged with other section headings.

Oxysterols

The present disclosure includes an osteogenic oxysterol (e.g., Oxy133), sterol, or diol and its ability to promote osteogenic differentiation in vitro. Oxy133 is a particularly effective osteogenic agent. In various applications, Oxy133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of Oxy133 is that it provides greater ease of synthesis and improved time to fusion when compared to other osteogenic oxysterols. Oxy133 is a small molecule that can serve as an anabolic therapeutic agent for bone growth, as well as a useful agent for treatment of a variety of other conditions.

One aspect of the application disclosure is a compound, named Oxy133, having the formula:

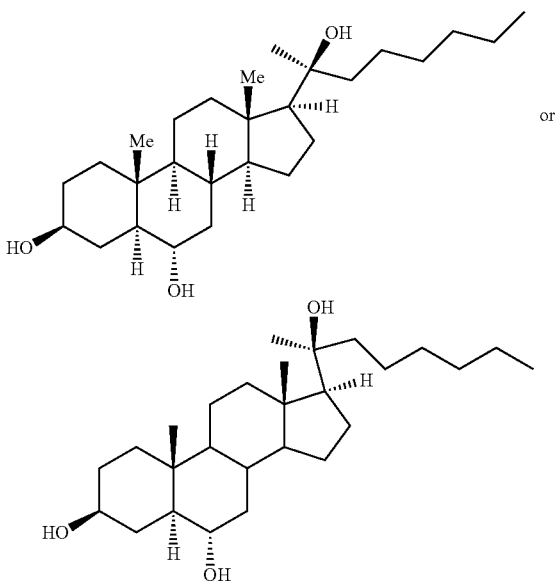

or a pharmaceutically acceptable salt, solvate or hydrate thereof. The Oxy133 may be used as a bioactive or pharmaceutical composition comprising Oxy133 or a pharmaceutically acceptable salt, solvate or hydrate thereof and a pharmaceutically acceptable carrier.

Another aspect of the disclosure is a method for inducing (stimulating, enhancing) a hedgehog (Hh) pathway mediated response, in a cell or tissue, comprising contacting the cell or tissue with a therapeutically effective amount of Oxy133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g. angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture, comprising administering to the subject an effective amount of a bioactive composition or pharmaceutical composition comprising Oxy133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In some embodiments, a composition comprising Oxy133 may include mesenchymal stem cells to induce osteoblastic differentiation of the cells at a targeted surgical area.

In various aspects, the Oxy133 can be administered to a cell, tissue or organ by local administration. For example, the Oxy133 can be applied locally with a cream or the like, or it can be injected or otherwise introduced directly into a cell, tissue or organ, or it can be introduced with a suitable medical device, such as a drug depot as discussed herein.

In some embodiments, the dosage of Oxy133, sterol, or diol is from approximately 10 pg/day to approximately 80 mg/day. Additional dosages of Oxy133, sterol, or diol include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day.

In addition to the compound Oxy133, sterol, or diol other embodiments of the disclosure encompass any and all individual stereoisomers at any of the stereocenters present in Oxy133, including diastereomers, racemates, enantiomers, and other isomers of the compound. In embodiments of the disclosure, Oxy133, sterol, oxysterol, diol may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, Oxy133, sterol, or diol includes one or more biological functions. That is, Oxy133, sterol, or diol can induce a biological response when contacted with a mesenchymal stem cell or a bone marrow stromal cell. For example, Oxy133, sterol, or diol may stimulate osteoblastic differentiation. In some embodiments, a bioactive composition including Oxy133 sterol, or diol may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Methods of Making Intermediary Diol

In some embodiments, the current disclosure provides a method for the preparation of an intermediary diol used in the production of Oxy133, as shown below. The diol may be used to promote bone growth as well. Previous methods of synthesis for Oxy133 produce were inefficient and not suitable for scale up manufacturing. Some stereoisomers of Oxy133 perform less optimally than others. The disclosed method is stereoselective and produces a high yield of the specific isomeric form of the diol shown below, which has been shown to produce an optimally effective isomeric form of Oxy133.

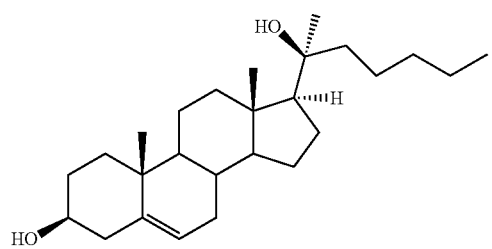 [SMILES: CCCCC[C@](C)(O)[C@H]1CCC2C3CC=C4C[C@@H](O)CC[C@]4(C)C3CC[C@@]21C]

Disclosed are multiple embodiments of reactions to synthesize the intermediary diol. The diol synthesized has the IUPAC designation (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Generally, the method of synthesizing the diol includes reacting pregnenolone, pregnenolone acetate or a pregnenolone derivative with an organometallic reagent to facilitate alkylation of the C17 position, as shown below:

Scheme 1

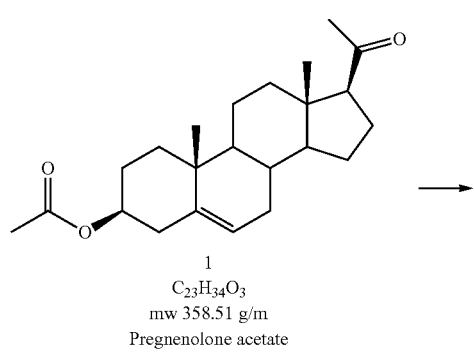

1
$C_{23}H_{34}O_3$
mw 358.51 g/m
Pregnenolone acetate

→

2
$C_{27}H_{46}O_2$
mw 402.67 g/m
Diol

In one embodiment, as shown above in scheme 1, pregnenolone acetate (formula 1) may be alkylated by an organometallic reagent to synthesize the intermediary diol, shown above as formula 2. In some embodiments, pregnenolone acetate is reacted with a Grignard reagent to facilitate alkylation of the C17 position on the pregnenolone acetate molecule. In some embodiments, n-hexylmagnesium chloride is used as the organometallic reagent.

Scheme 2

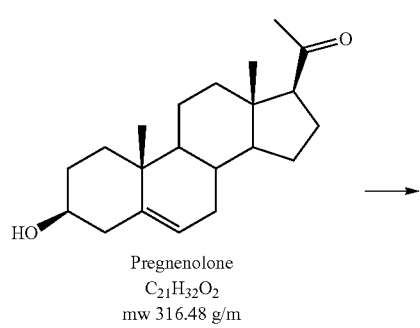

Pregnenolone
$C_{21}H_{32}O_2$
mw 316.48 g/m

→

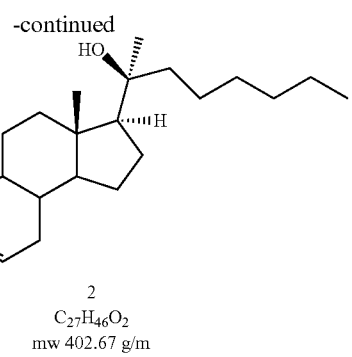

2
$C_{27}H_{46}O_2$
mw 402.67 g/m

In some embodiments, as shown above as scheme 2, pregnenolone is reacted with a Grignard reagent such as n-hexylmagnesium chloride to facilitate alkylation of the C17 position of the pregnenolone molecule to form the intermediary diol shown as formula 2.

The method of synthesizing the intermediary diol (formula 2) or (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol is stereoselective and produces a high yield of the diol. For example, in some embodiments, the yield of the desired stereoisomer of the diol is between about 60% and about 70%. In some embodiments, the yield of the desired stereoisomer of the diol is between about 50% and about 60%. However, it is contemplated that the percent yield may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the alkylation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, pregnenolone or pregnenolone acetate is used as a starting reactant. However, in other embodiments, derivatives of pregnenolone acetate may be used. For example, other specific examples of compounds which could be used in the present disclosure include: pregnenolone sulfate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3β-hydroxypregn-5-en-20-one sulfate, 3-hydroxy-19-norpregna-1,3,5(10)-trien-20-one, 3-hydroxy-19-norpregna-1,3,5(10),6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, 21-thiol esters of pregnenolone sulfate, pyridinium, imidazolium, 6-methylpregnenolone sulfate, 6,16α-dimethylpregnenolone sulfate, 3β-hydroxy-6-methylpregna-5,16-dien-20-one sulfate, 3β-hydroxy-6,16-dimethylpregna-5,16-dien-20-one sulfate, 3jβ-hydroxypregna-5,16-dien-20-one sulfate, diosgenin sulfate, 3β-hydroxyandrost-5-en-17β-carboxylic acid methyl ester sulfate, 3α hydroxy-5β-pregnan-20-one formate, 3α-hydroxy-5β-pregnan-20-one hemioxalate, 3α-hydroxy- 5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol-3-methyl ether, 17-deoxyestrone, and 17β-hydroxyestra-1,3,5(10)-trien-3-yl carboxymethyl ether.

In some embodiments, the organometallic comprises n-hexylmagnesium chloride. However, in some embodiments, the alkylation reaction may be carried out with the use of an alkyllithium, such as, for example, n-hexyllithium. In various embodiments, the organometallic includes an alkyl halide. For example, the organometallic reagent may have the following formula:

$$R—Mg—X,$$

where Mg comprises magnesium, X comprises chlorine, bromine, fluorine, iodine, or astatine and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a (C1-C20) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

Alternatively, the organometallic may comprise the formula:

$$R—Li,$$

where Li comprises lithium and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a ($C_1$-$C_{20}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

In some embodiments, the alkylation reaction is exothermic and the reaction vessel may be temperature controlled to maintain optimal reaction kinetics. In some embodiments, the exothermic reaction releases about 1000 BTU per pound of solution. Due to the strongly exothermic nature of the reaction, the Grignard reagent therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 15° C., 10° C., 5° C. or 1° C. In some embodiments, the reaction vessel is maintained at about 0° C. during the alkylation reaction to form the intermediary diol of formula 2.

In various embodiments, the diol of formula 2 is synthesized along with byproducts and can be purified. For example, the resulting diol of formula 2 may be a byproduct of a diastereomeric mixture. In various embodiments, the diol of formula 2 may be isolated and purified. That is, the diol of formula 2 can be isolated and purified to the desired purity, e.g., from about 95% to about 99.9% by filtration, centrifugation, distillation, which separates volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. The diol may be purified by contacting it with organic and/or inorganic solvents, for example, THF, water, diethyl ether, dichloromethane, ethyl acetate, acetone, n,n-dimethylformamide, acetonitrile, dimethyl sulfoxide, ammonia, t-butanol, n-propanol, ethanol, methanol, acetic acid, or a combination thereof.

In various embodiments, the alkylation step and the purification step take place in the same reaction vessel.

In some embodiments, the diol is quenched with aqueous ammonium chloride or acetic acid to reduce the amount of anions present and neutralize the reaction and separated from the resulting organic layer. The separated residue is recovered by evaporation and purified by silica gel column chromatography.

The diol may be anhydrous or in the monohydrate form. However, in other embodiments the purified diol may be crystallized in other hydrous forms, such as, for example, a dihydrate, a hemihydrate, a sesquihydrate, a trihydrate, a tetrahydrate and the like, as well as the corresponding solvated forms. In other embodiments, the purified diol is crystallized as a co-crystal or a pharmaceutically acceptable salt.

Methods of Making Oxy133

In some embodiments, the current disclosure provides a method for the preparation of an Oxy133, as shown below. Previous methods of synthesis for Oxy133 produce diastereomeric mixtures of Oxy133 intermediates which require purification methods to separate. As discussed above to form the intermediary diol, the disclosed method is stereoselective and produces a high yield of the specific isomeric forms of Oxy133. The formula of Oxy133 is shown below.

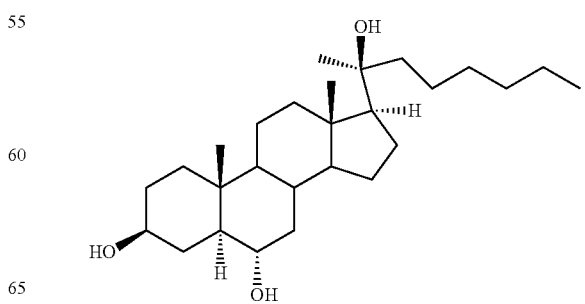

Disclosed are multiple embodiments of reactions to synthesize Oxy133. Oxy133 has the IUPAC designation (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol. Oxy133 has previously been synthesized through a complex process not suitable for scale-up as shown below:

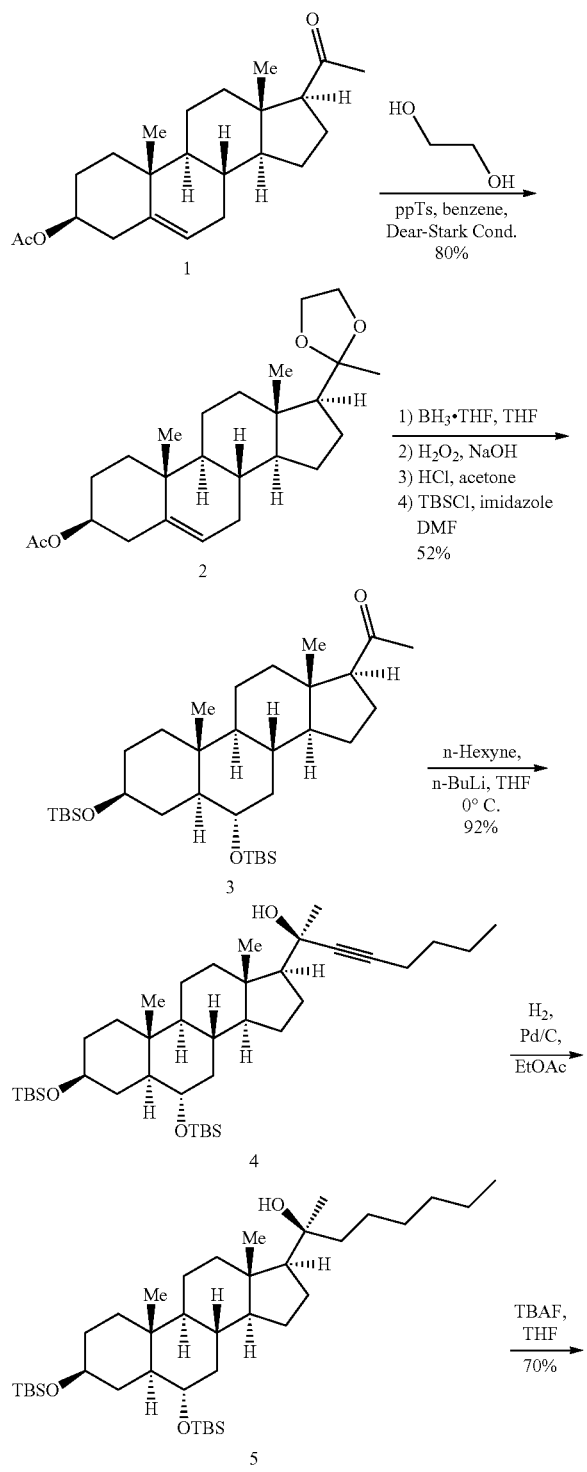

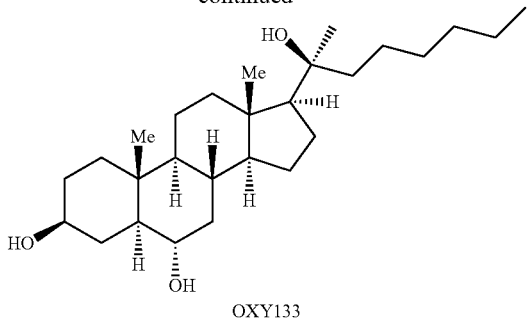

OXY133

However, the reaction has difficulty being carried out in a single container. The reaction shown above involves more reagents to carry out reaction steps (e.g., blocking and deprotection groups and steps) which have an adverse environmental impact. Additionally, the known methods involve reagents that are expensive and often difficult to obtain. Further, the method shown in Scheme 3 gives relatively low yields, has more degradation products, impurities and creates many toxic byproducts.

Generally, the method of synthesizing Oxy133 as disclosed herein includes reacting the diol synthesized as described herein with borane in the reaction shown below:

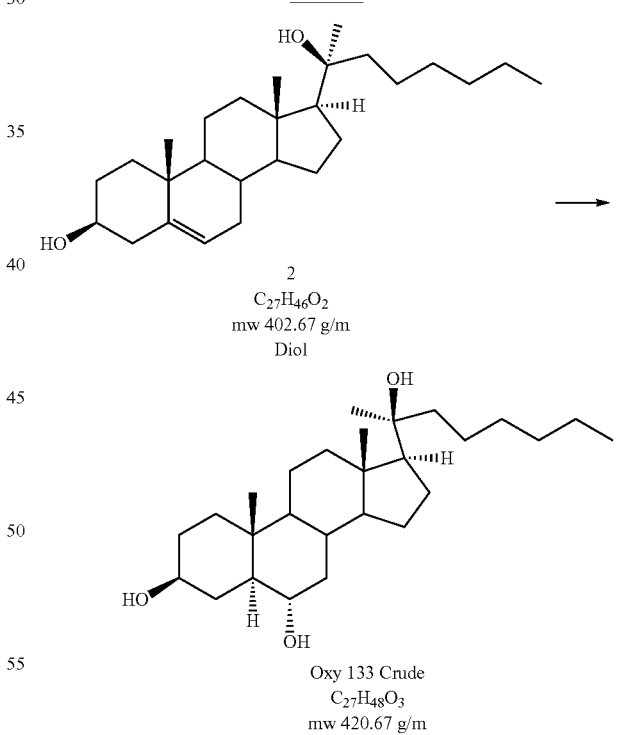

In some embodiments, crude and unpurified Oxy133 is produced through a hydroboration and oxidation reaction of the intermediary diol having formula 2 in reaction scheme 4. Borane compounds that can be used in the reaction include $BH_3$, $B_2H_6$, $BH_3S(CH_3)2$ (BMS), borane adducts with phosphines and amines, e.g., borane triethylamine; monosubstituted boranes of the form $RBH_2$ where R=alkyl and halide, monoalkyl boranes (e.g., IpcBH2, monoisopinocampheylborane), monobromo- and monochloro-borane, complexes of monochloroborane and 1,4-dioxane, disubstituted boranes including bulky boranes, such as for example, dialkylborane compounds such as diethylborane, bis-3-methyl-2-butylborane (disiamylborane), 9-borabycyclo[3,3,1]nonane (9-BBN), disiamylborane (Sia2BH), dicyclohexylborane, Chx2BH, trialkylboranes, dialkylhalogenoboranes, dimesitylborane $(C_6H_2Me_3)_2BH$, alkenylboranes, pinacolborane, or catecholborane or a combination thereof.

Briefly, a hydroboration and oxidation reaction is a two-step reaction. The boron and hydrogen add across the double bond of an alkene to form a complex with the alkene. Thus the boration phase of the reaction is stereoselective and regioselective. The oxidation phase of the reaction involves basic aqueous hydrogen peroxide to furnish a hydroxyl substituent in place of the boron. See Vollhart, K P, Schore, N E, 2007, Organic Chemistry: Structure and Function, Fifth Ed., New York, N.Y., Custom Publishing Company. Thus, the intermediary diol having formula 2 is reacted with borane and hydrogen peroxide to form crude Oxy133. In some embodiments, the step of forming crude Oxy133 takes place in the same reaction vessel as the alkylation reaction. In other embodiments, the step of forming crude Oxy133 takes place in a different reaction vessel as the alkylation reaction.

The hydroboration-oxidation step of the synthesis of Oxy133, like the step of forming the intermediary diol, is stereoselective and produces a high yield. For example, in some embodiments, the percent yield of crude Oxy133 may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the hydroboration-oxidation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the hydroboration-oxidation reaction is exothermic and the reaction vessel can be temperature controlled to maintain optimal reaction kinetics. Specifically, the oxidation phase is extremely exothermic. Due to the strongly exothermic nature of the reaction, the hydrogen peroxide therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 10° C., 5° C., 1° C. or 0° C. In some embodiments, the reaction vessel is maintained at about −5° C. during the hydroboration-oxidation reaction.

In certain embodiments the diol can have a percent crystallinity of a salt, hydrate, solvate or crystalline form of diol to be at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of diol appears to be crystalline as best can be determined using methods known in the art. Accordingly, therapeutically effective amounts of diol can include amounts that vary in crystallinity. These include instances where an amount of the crystallized diol in a solid form is subsequently dissolved, partially dissolved, or suspended or dispersed in a liquid.

Purification of Oxy133

In some embodiments, the crude Oxy133 can be separated from the reaction mixture prior to purification. In some embodiments, an organic solvent such as dichloromethane is added to the crude Oxy133 reaction mixture and the resulting organic layer is separated. Once separated, the crude Oxy133 exists as a semi-solid viscous mass. The crude Oxy133 may be dissolved by any suitable means (e.g., dichloromethane, etc.) and placed into a silica gel column with an organic solvent, such as methanol-ethyl acetate, to solvate the crude Oxy133. In some embodiments, the crude Oxy133 may be crystallized or recrystallized. In some embodiments, purified Oxy133 is formed by recrystallizing the crude Oxy133 in a 3:1 mixture of acetone/water, as shown below:

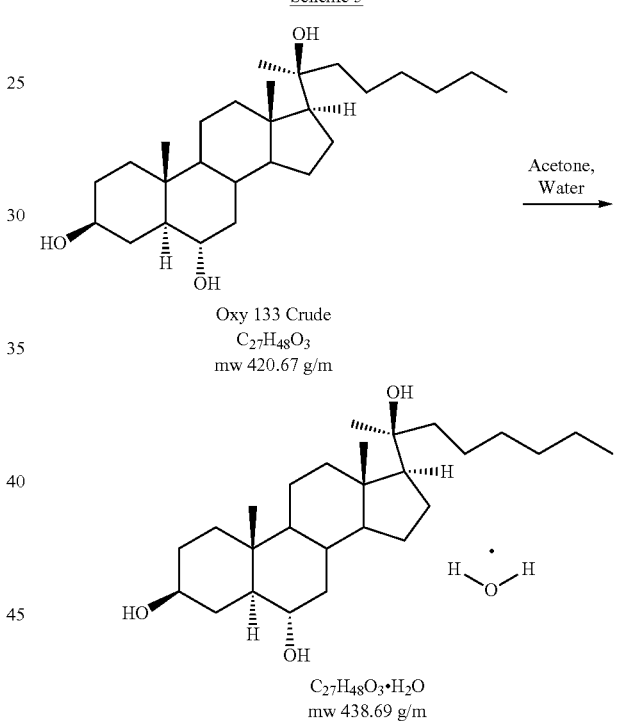

Scheme 5

As shown above, upon crystallization, the purified Oxy133 forms a hydrate. However, it can be in the anhydrous form. In some embodiments, the percent crystallinity of any of the crystalline forms of Oxy133 described herein can vary with respect to the total amount of Oxy133.

In certain embodiments the OXY133 can have a percent crystallinity of a salt, hydrate, solvate or crystalline form of Oxy133 to be at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of Oxy133 appears to be crystalline as best can be determined using methods known in the art. Accordingly, therapeutically effective amounts of Oxy133 can include amounts that vary in crystallinity. These include instances where an amount of the crystallized Oxy133 in a solid form is subsequently dissolved, partially dissolved, or suspended or dispersed in a liquid.

In one embodiment, the purified Oxy133 is crystallized as a monohydrate. However, in other embodiments the purified Oxy133 may be crystallized in other hydrous forms, such as, for example, a dihydrate, a hemihydrate, a sesquihydrate, a trihydrate, a tetrahydrate and the like, as well as the corresponding solvated forms. In other embodiments, the purified Oxy133 is crystallized as a co-crystal or a pharmaceutically acceptable salt.

In some embodiments, the reaction mixture containing the crude Oxy133 may be solidified by mixing with heptanes. The product may subsequently be filtered and suspended in methylene chloride. In some embodiments, the crude Oxy133 may be filtered from the suspension and crystallized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the crude Oxy133 may be isolated and purified by any other traditional means. That is, the crude Oxy133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. In various embodiments, the hydroboration-oxidation step and the purification step take place in the same reaction vessel. In various embodiments, the alkylation step, the hydroboration-oxidation step and the purification step take place in the same reaction vessel.

The method of synthesizing the intermediary diol (formula 2) is stereoselective and produces a high yield of Oxy133. For example, in some embodiments, the yield of the purified Oxy133 is between about 20% and about 99%. In some embodiments, the yield of the purified Oxy133 is between about 20% and about 80%. In some embodiments, the yield of the purified Oxy133 is between about 25% and about 70% or about 28%. However, it is contemplated that the percent yield may be higher or lower than these amounts.

In some embodiments, the purified Oxy133 is formed in crystal form via crystallization, which separates the Oxy133 from the liquid feed stream by cooling the liquid feed stream or adding precipitants which lower the solubility of byproducts and unused reactants in the reaction mixture so that the Oxy133 forms crystals. In some embodiments, the solid crystals are then separated from the remaining liquor by filtration or centrifugation. The crystals can be resolubilized in a solvent and then recrystallized and the crystals are then separated from the remaining liquor by filtration or centrifugation to obtain a highly pure sample of Oxy133. In some embodiments, the crystals can then be granulated to the desired particle size.

In some embodiments, the purity of the Oxy133 obtained is verified through nuclear magnetic resonance or mass spectroscopy. As shown in FIGS. 2-5, 1H NMR, 13C NMR, infrared spectroscopy, and mass spectroscopy analysis indicated that the Oxy133 product had high purity (e.g., having 98% to about 99.99% by weight purity).

In some embodiments, the crude Oxy133 can be purified where the purified Oxy133 is formed in crystalized form in a solvent and then removed from the solvent to form a high purity Oxy133 having a purity of from about 98% to about 99.99%. In some embodiments, the Oxy133 can be recovered via filtration or vacuum filtration before or after purification.

Use of Analytical Method for the Separation and Detection of Oxysterols

OXY133 and its related impurities are non-volatile compounds which lack a chromophore making chromatography insufficient for determining the purity of a sample comprising OXY133. A reproducible chemical synthesis of OXY133 and established analytical methods to characterize the OXY133 product can be important activities during the development process.

A process for determining the purity of OXY133 has been unexpectedly found which includes subjecting an HPLC eluent comprising OXY133 and OXY133 impurities to further analysis with a charged aerosol detector (CAD). This process can separate and quantify OXY133 in the presence of known impurities to a purity of at least 96.9% w/w or w/v based on the total weight of the composition. CAD is highly sensitive and provides a response independent of chemical structure.

Figure 8:
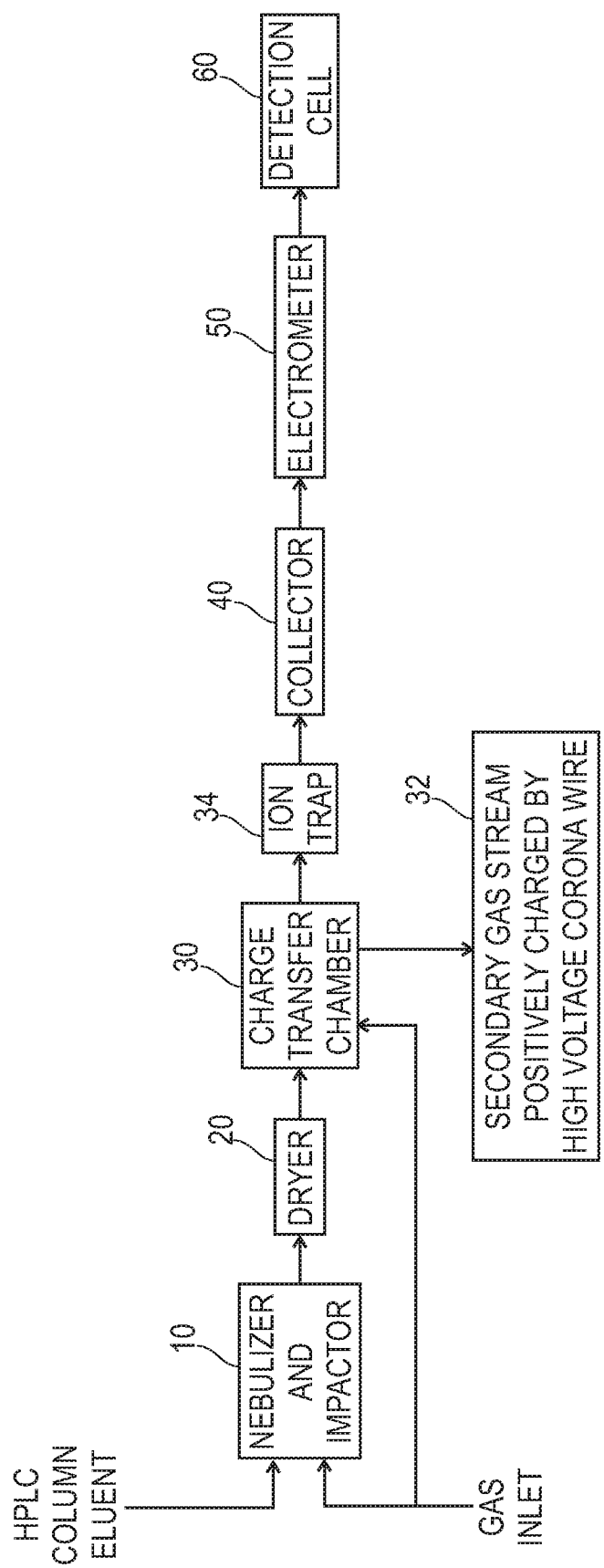
FIG. 8 is a block diagram of an embodiment illustrating how a charged aerosol detector (CAD) works.

A flow diagram and process steps of a CAD detector is illustrated in FIG. 8. There are several CAD manufacturers including, for example, Thermo Scientific™ Dionex™ Corona™ CAD detectors. A CAD detector useful for liquid chromatography applications is described in U.S. Pat. No. 6,568,245, incorporated herein by reference as if set forth in full.

Generally, a CAD detector includes a corona discharge source controlled to selectively charge the non-volatile residue particles of an aerosol. The aerosol initially is composed of droplets of a liquid sample (e.g., containing OXY133), with the non-volatile residue particles resulting from droplet evaporation. The selectively charged residue particles, each carrying a charge in proportion to its size, are collected at a conductive filter. The electrical current along a conductor coupled to the filter is measured repeatedly or continuously to provide an indication of concentrations of the non-volatile material. Preferably, a pneumatic nebulizer is used to generate the aerosol. When used in a liquid chromatography system, the detector can yield several separated areas of relatively high electrical current, corresponding to concentrations of several different analytes in the liquid sample.

In some embodiments, a CAD detector can be used after an OXY133 containing sample is first subjected to HPLC. In FIG. 8, the HPLC eluent comprising an OXY133 compound and a volatile mobile phase, is nebulized with a nebulizer 10 to form an aerosol of liquid droplets. Nebulizer 10 is disposed to receive a liquid incorporating non-volatile material, and adapted to nebulize at least a portion of the liquid to generate an aerosol stream composed of droplets of the liquid suspended in a carrier gas, the droplets tending to evaporate whereby the aerosol stream at a selected location downstream of the nebulizer is composed of residual particles of the non-volatile material suspended in the carrier gas.

Useful nebulizers include pneumatic, electrostatic, thermospray, ultrasonic nebulizers and hybrid devices, for example electrically assisted pneumatic nebulizers. Generally, the incoming HPLC eluent is first nebulized with nitrogen or an air carrier gas to form droplets that are then passed through a dryer 20 that removes the volatile mobile phase and produces OXY133 residue or analyte particles. As the droplets proceed along dryer 20 they evaporate, to the point where the aerosol, rather than being composed of the liquid droplets, is composed of residue particles of a non-volatile material formerly dissolved in the solution. The stream of residue particles is then carried to a charge transfer chamber 30 where it is met by a secondary gas stream positively charged by a high-voltage platinum corona wire 32. The amount of charge transferred to the stream of residue particles is related to the particle size. The stream of positively charged residue particles is further transferred to collector 40 where the total charge imparted to the residue particles can be measured with an electrometer 50, which generates a signal in direct proportion to the quantity of non-volatile residue or analyte particles detected. This signal is then processed by a detection cell 60 and stored to generate a chromatogram depicting the variation in the intensity of detected analyte as a function of chromatographic retention time. In some embodiments, the CAD system illustrated in FIG. 8 also includes an ion trap 34 positioned after the charge transfer chamber, which functions to remove negatively charged high-mobility particles.

Nebulization is important in the CAD process because in this step volatile mobile phases can be used to carry the liquid droplets to the next step. Examples of volatile mobile phases useful in the processes of this application include without limitation aqueous/organic solvents (water/methanol/acetonitrile mixtures), which includes in some embodiments, volatile buffer additives such as formic acid, acetic or trifluoroacetic acid, and ammonium acetate, similar to mass spectrometry (MS) mobile phase requirement.

In some embodiments, the measurement of purity of OXY133 and/or OXY133 monohydrate can be achieved by using a software program connected to the detection cell 60 and executable by a suitable processor, not shown in FIG. 8. An example of useful software for the methods described in this disclosure is Empower 3 software.

The International Conference of Harmonization of Technical Requirements for Registration of Pharmaceuticals for Human Use (ICH), an international regulatory agency, has reporting thresholds for impurities for new drug substances. For new drug substances the reporting threshold can vary from about 0.03% w/w or w/v based on the total weight of the composition for drugs having a daily dose higher than 2 g to about 0.05% w/w or w/v based on the total weight of the composition for drugs having an average daily dose below 2 g. Accordingly, a main goal in the quality control of an active pharmaceutical ingredient (API) is developing a method to detect, control and quantify its impurities.

In various embodiments, CAD analysis of an HPLC eluent containing OXY133 and OXY133 related impurities and/or other compounds can be used to separate and quantify OXY133 in the presence of known impurities during the analytical method development (AMD) phase required to validate ICH quality control guidelines. Performance characteristics investigated to determine the AMD efficacy for determining the purity of OXY133 include solvent system, analyte response, lower limit of quantitation (LOQ), and intermediate precision as discussed in more detail below. Following the measurement of the purity of OXY133 or OXY133 monohydrate in a sample containing the same and the determination that a sample is free of impurities or substantially free of impurities, including or not limited to from about 95%, 95.5% 96%, 96.5%, 97%, 97.5%, 98%, 98.5%, 99%, 99.5%, or 99.9% w/w or w/v pure or free from impurities. The measurement results are recorded and communicated to technicians, clients, and/or government agencies, for example. In certain embodiments, computers will be used to communicate such information to interested parties, such as, technicians, clients, and/or government officials, including but not limited to the FDA.

Solvent System

High purity solvents were used to reduce noise and baseline drift. Since the CAD process involves nebulization to remove the mobile phase, volatile mobile phases were used. Water/methanol/acetonitrile mixtures with and without formic acid, were evaluated. Linearity and precision were run at the same time with solutions prepared in two different solvents. A comparison of the linearity and precision runs is shown in Table 1, below.

TABLE 1

Comparison of Linearity and Precision Runs

| Sample Set Name | Solution Diluent | Range (ug/mL) | Coefficient of Determination ($r^2$) |
|---|---|---|---|
| Test 14 | Water/ACN, 1:1 | 20.50 to 500.70 | 0.99505 |
| Test 15 | ACN only | 0.514 to 61.62 | 0.99519 |

| Sample Set Name | Solution Diluent | Concentration (ug/mL) | % RSD | Mean Area (n = 6) | Mean s/n |
|---|---|---|---|---|---|
| Test 14 | WateriACN, 1:1 | 61.62 | 2.1 | 1351990 | 141 |
| Test 15 | ACN only | 10.27 | 2.1 | 1004157 | 198 |

Analyte Response

Figure 9:
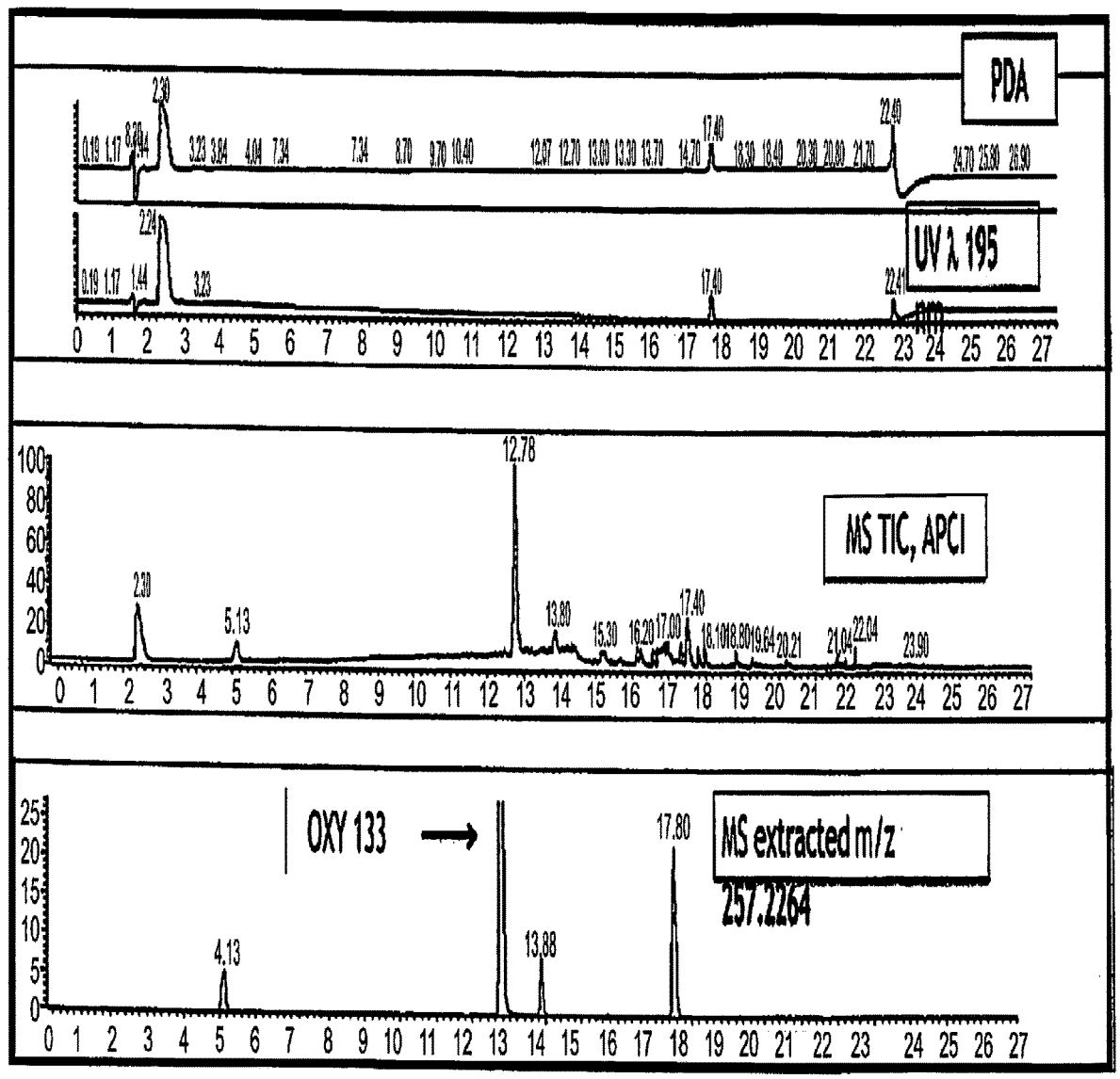
FIG. 9 is a graphic illustration of linear photodiode array detector (PDA) trace, ultraviolet (UV) channel at 195 nm, mass spectrometry total ion chromatography (MS TIC) and MS extracted mass to charge ratio (m/z) 257.2264.

To determine analyte response and solvent effects during AMD, a flow injection analysis (FIA) experiment was performed by injecting the OXY133 in mobile phase without the column in line. The AMD system included multiple detectors in series configuration. The HPLC/DAD/MS scans with the proposed analytical column detected distinct Oxy133 detection profiles as illustrated by a PDA trace, followed by UV Channel @ 195 nm, then the MS TIC followed by the extracted m/z 257.2264 as illustrated in FIG. 9.

Lower Limit of Quantitation

Figure 10:
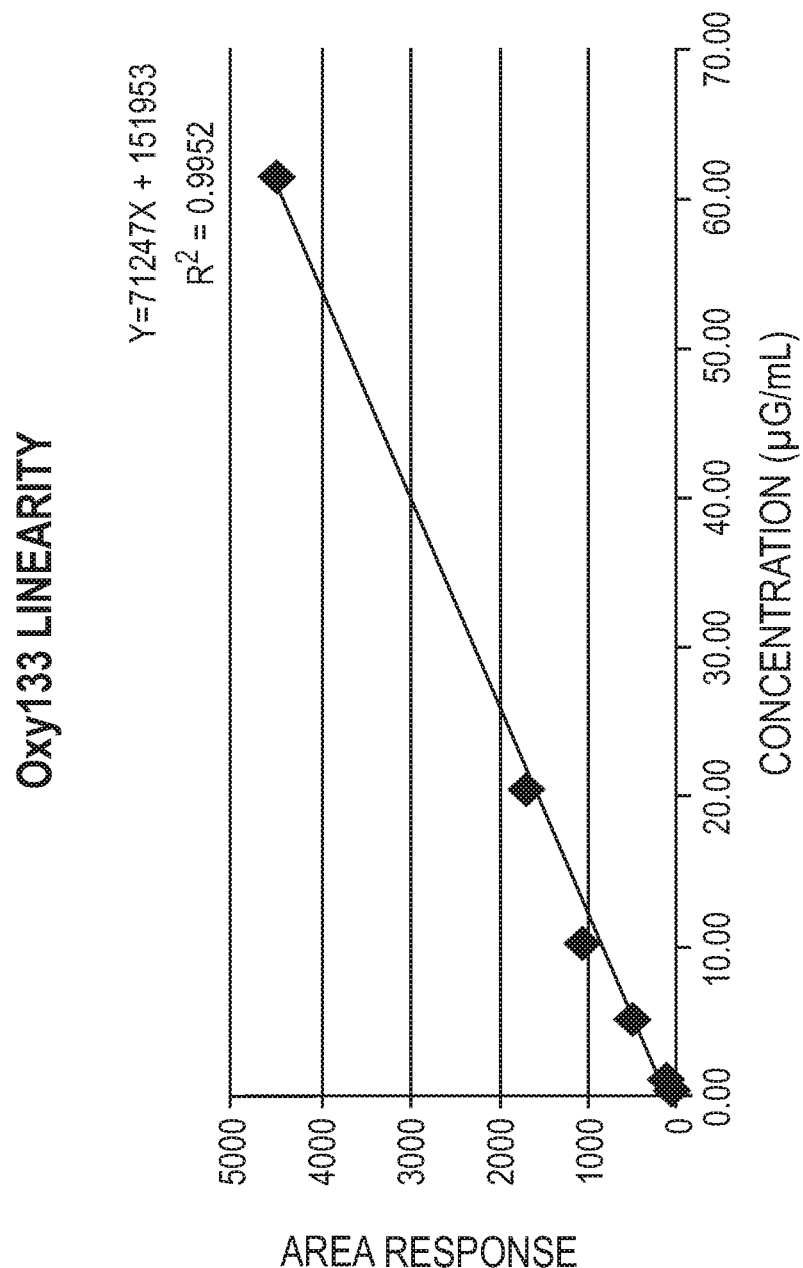
FIG. 10 is a graphic illustration of linearity of OXY133 from 0.50 μg/mL to 61 μg/mL.

To determine the lowest detection limit (sensitivity) for Oxy133, a lower linearity curve to determine the lowest Quantitation Level (QL) concentration that can be obtained on the CAD system detection of Oxy133 from 0.50/mL to 61 ug/mL was determined as depicted in FIG. 10.

Intermediate Precision

A CAD analysis comparison was performed on two HPLC-CAD systems with optimized water/methanol mobile phase system with same type column (XBridge Phenyl, 4.6×150 mm, 3.5µ particle size) but different columns. Each system independently produced acceptable system suitability results meeting resolution (Rs)>1.2 and RSD<2%.

AMD Performance Parameters for HPLC/CAD

During AMD, variations in CAD response due to mobile phase composition were investigated. Variations in response due to mobile phase composition showed no interference and the low level linearity was within an acceptable range. Precision, LOQ and system suitability targets for OXY133 were evaluated in accordance with ICH validation guidelines and found to meet requirements.

The method of separating and quantifying OXY133 in the presence of known impurities was conducted on an HPLC instrument configured with a C18 column with dimensions 4.6×150 mm, a 3.5 micron particle size, column temperature at 40° C. and a gradient flow rate at 1.0 ml/min for 27 minutes. The CAD conditions were set such that the nitrogen flow was 1.53 ml/min with gas pressure at 35 psi and the range set to 200 pA and the nebulizer temperature was off or at 35° C. The parameters for the HPLC-CAD system useful for the process of this application are summarized in Tables 2 and 3 below:

TABLE 2

HPLC Parameters

| Column | XBridge Phenyl, 4.6 × 150 mm, 3.5µ particle size |
|---|---|
| Column Temp | 40° C. |
| Flow Rate | 1.0 mL/min |
| Mobile Phase A | Water |
| Mobile Phase B | Methanol |

| Gradient | Time (mm) | % A | % B |
|---|---|---|---|
| | 0.00 | 35 | 65 |
| | 18.00 | 20 | 80 |
| | 25.00 | 0 | 100 |
| | 29.00 | 0 | 100 |
| | 29.01 | 35 | 65 |
| Injection Vol. | 10 µL | | |

TABLE 3

CAD Settings

| Nitrogen Flow | 1.53 mL/min |
|---|---|
| Gas Pressure | 35 psi |
| Filter | None |
| Range | 100 pA |
| Offset | 0 |
| Nebulizer Temperature | Off or 35° C. |

In some embodiments, the current disclosure provides an assay method for determining the purity of a sample of OXY133, the method comprising providing an HPLC eluent including OXY133, OXY133 impurities and a mobile volatile phase; generating an aerosol of liquid droplets from the HPLC eluent; drying the droplets to obtain residue particles of OXY133; contacting the OXY133 residue particles with an ion stream which applies a size-dependent electrical charge to each of the residue particles to generate an electrical signal having a level proportional to the amount of charged residue particles of OXY133; and measuring the electrical signal to determine the purity of OXY133 in the sample. In other embodiments, OXY133 comprises OXY133 monohydrate.

In yet other embodiments, the method of this disclosure further comprises transferring the charged residue particles of OXY133 to a collector and measuring the electrical signal with an electrometer. In other aspects, a nebulizer is utilized to generate the aerosol of liquid droplets from the HPLC eluent.

In various aspects, the assay method of the present disclosure can be used to separate OXY133 monohydrate, from diastereomer D1, diastereomer D2 or other OXY133 monohydrate impurity, for example $C_{27}H_{46}O_2$ diol used to synthesize OXY133 monohydrate. In various embodiments, the assay method of this disclosure can detect OXY133 monohydrate impurities from about 0.03% to about 0.05% w/w or w/v. The resolution of the OXY133 peak and the D1 diastereomer that can be achieved using the assay method of this disclosure can be >0.8. In many embodiments, the limit of detection of the OXY133 monohydrate is about 0.01% or 1 ng. Further, the purity of OXY133 monohydrate that can be achieved by using the assay method of this disclosure is at least 96.9%.

In other aspects, the mobile volatile phase useful with the CAD detector of the method of this disclosure comprises acetonitrile, a mixture of acetonitrile and water, a mixture of water and methanol or a mixture of water, methanol and acetonitrile. In yet other aspects, in the method for the determining purity of a sample of OXY133, after OXY133 is recovered it is placed in a pharmaceutical formulation for example, tablet, capsule, injection, depot etc.

In various other embodiments, a method is provided for separating OXY133 monohydrate from a drug sample, the method comprising providing an OXY133 monohydrate reference standard; providing the drug sample having a concentration equivalent to OXY133 monohydrate reference standard; determining the amount of OXY133 monohydrate in the reference standard by HPLC-CAD; determining the amount of OXY133 monohydrate in the drug sample by HPLC-CAD; and comparing the amount of OXY133 monohydrate in the drug sample to the amount of OXY133 monohydrate in the reference standard. In some embodiments, in the method of this disclosure the reference standard concentration is present in an amount of at least 500 µg/mL containing OXY133 and/or OXY133 monohydrate. In other aspects, the drug sample is prepared in a solution of acetonitrile:tetrahydrofuran, 1:1, volume by volume. In yet other aspects, the drug sample comprises a mobile volatile phase from the HPLC-CAD, which is 100% water or 100% methanol.

Figure 11:
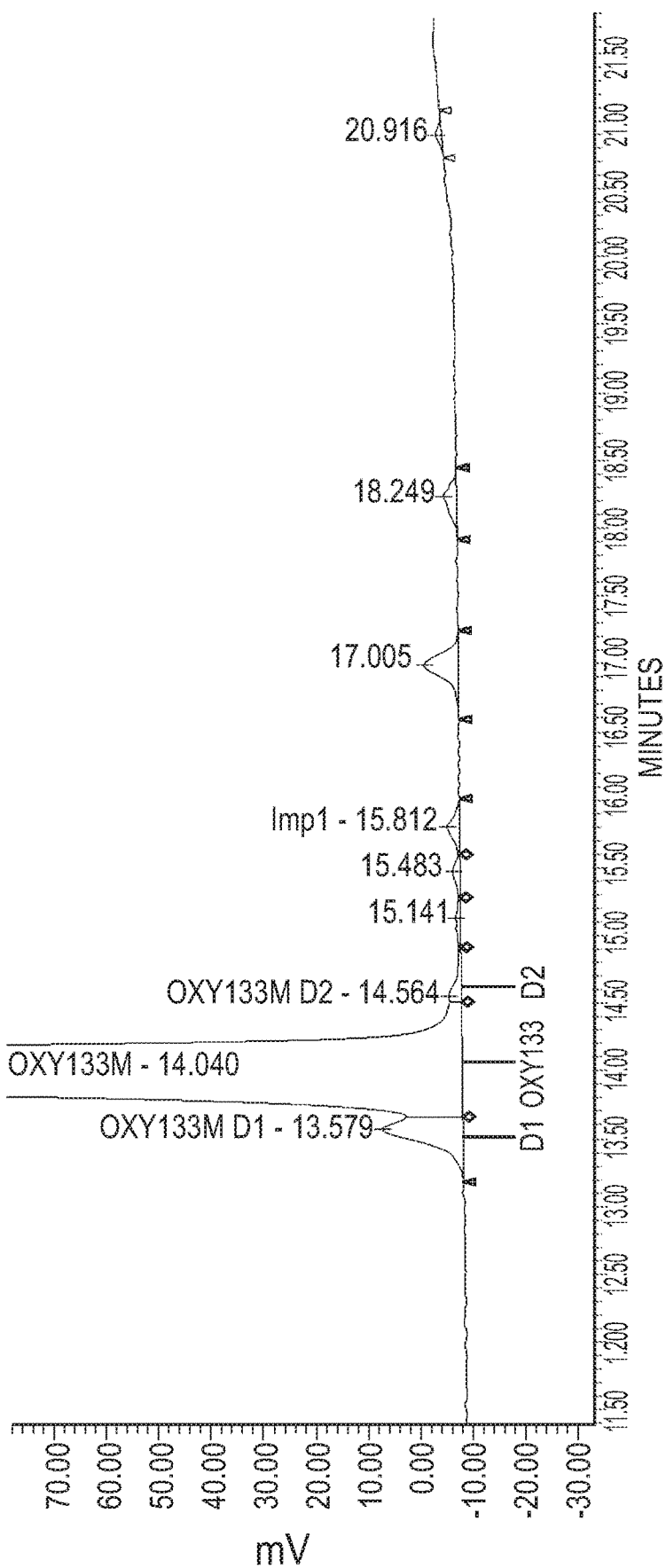
FIG. 11 is a graphic illustration of a chromatogram of OXY133 monohydrate Reference Standard at 500 μg/mL.
Figure 12:
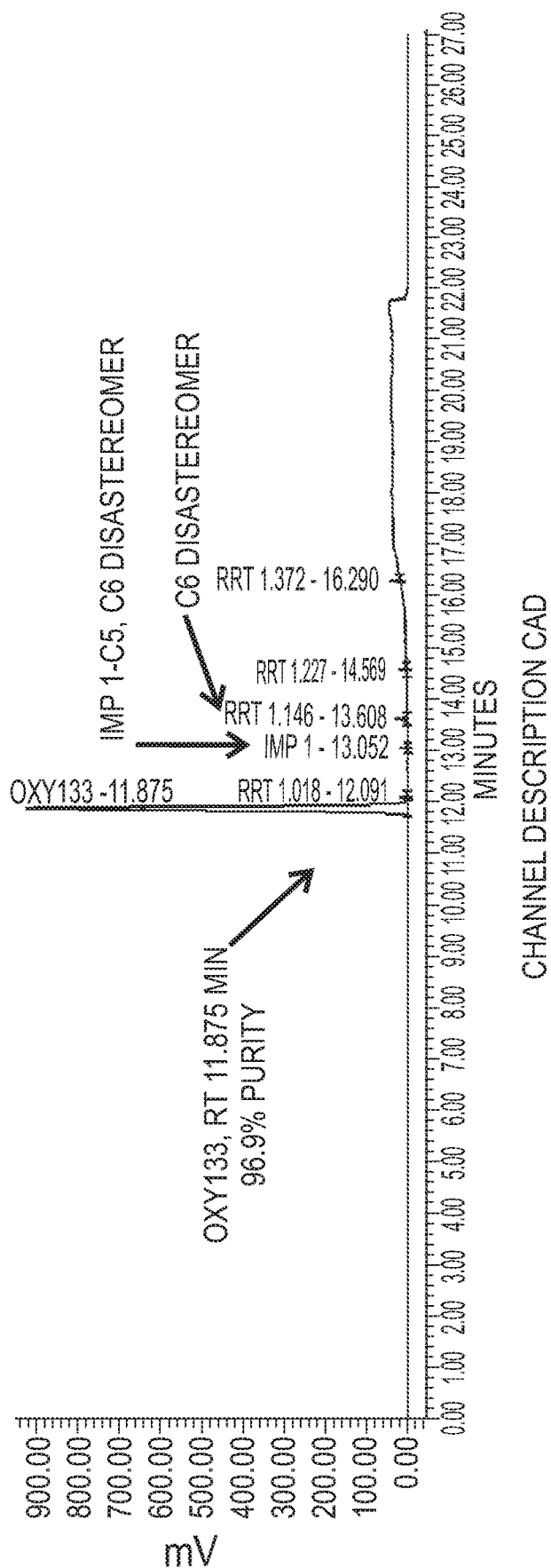
FIG. 12 is a purity profile of OXY133 generated by HPLC/CAD method.

In other embodiments, the OXY133 monohydrate subjected to separation by HPLC-CAD comprises diastereomer D1, diastereomer D2, $C_{27}H_{46}O_2$ diol or OXY133 monohydrate impurity 1. When detected by the method of this disclosure, these known compounds related to OXY133 or OXY133 monohydrate exhibit the following approximate retention and relative retention times as illustrated in Table 4 and depicted in FIG. 11:

TABLE 4

Compounds Related to OXY133

| Component and Related Compound | Approximate Retention Time (minutes) | Approximate Relative Retention Time (minutes) |
|---|---|---|
| Oxy133 (API) | 14.0 | 1.00 |
| Impurity 1 | 15.8 | 1.12 |
| Diol | 20.2 | 1.42 |
| Oxy133 Diastereomer 1 (D1) | 13.6 | 0.97 |
| Oxy133 Diastereomer 2 (D2) | 14.6 | 1.04 |

In various other embodiments, a method is provided for determining the purity in a sample of OXY133 monohydrate, the method comprising: providing an oxysterol by reacting a diol having the formula:

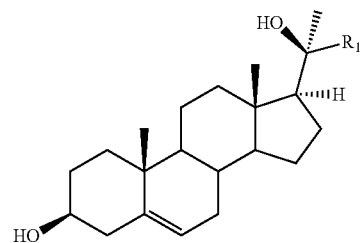

with borane, hydrogen peroxide and tetrahydrofuran to form the oxysterol or a pharmaceutically acceptable salt, hydrate or solvate thereof having the formula:

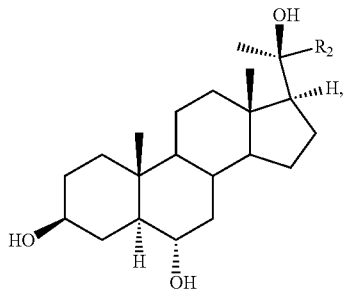

wherein R1 and R2 comprise a hexyl group and the diol comprises (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol and the hydrate is an OXY133 monohydrate; subjecting the monohydrate to HPLC to obtain an eluent comprising OXY133 monohydrate, impurities of OXY133 monohydrate and a volatile mobile phase; charging the HPLC eluent into a CAD detector to determine the purity of OXY133 monohydrate.

In various other aspects a method for testing the suitability of an HPLC-CAD system to analyze a drug sample comprising OXY133 monohydrate is provided, the method comprising: running diluent blank injections to obtain a baseline free of interferences in the region of OXY133 monohydrate; running at least one reference Standard Solution to obtain a relative standard deviation of ≤2.0%; running at least one solution comprising a quantitation level OXY133 monohydrate solution, a quantitation level impurity 1, a quantitation level $C_{27}H_{46}O_2$ diol solution; running a first Bracketing Reference Standard Solution; running at least one sample solution; running a second Bracketing Reference Standard Solution. In yet other aspects, the OXY133 monohydrate in the reference standard and the first and second Bracketing Reference Standards have a resolution ≥0.8 for diastereomer D1.

In various embodiments, the quantitation level injections have a visible peak having a signal to noise ratio ≥10. In yet other embodiments, the area of the Bracketing Reference Standard is within ±2% of the mean of the six reference Standard Solutions utilized to test the HPLC-CAD system suitability for AMD. In several embodiments, the quantitation level injections of Impurity 1 and $C_{27}H_{46}O_2$ diol show a visible peak for each compound at a concentration of 0.5 µg/mL free from interference in the region of analyte OXY133 peak. System precision can be demonstrated throughout the above runs by injecting a reference standard after at least every six sample injections. These standards are identified as Bracketing Reference Standards (BRS). Additionally, each run can end with a BRS injection.

These and other aspects of the present application will be further appreciated upon consideration of the following Examples, which are intended to illustrate certain particular embodiments of the application but are not intended to limit its scope, as defined by the claims.

EXAMPLES

Example 1

Preparation from Pregnenolone Acetate 8.25 mL n-hexylmagnesium chloride (2 M, 16.5 mmol) in THF was added to a solution of pregnenolone acetate in THF under vigorous electromagnetic stirring and ice bath cooling. The pregnenolone acetate solution contained 1.79 g compound 1, pregnenolone acetate, (5 mmol) in 4.5 mL THF. The addition took place over 2 minutes. After addition was completed, the mixture was stirred at room temperature for 3.5 hours, at which point the mixture had turned to a gel. The gel was then digested with a mixture of saturated aqueous $NH_4Cl$ and MTBE (methyl tertiary-butyl ether). The organic layer was separated, washed with water three times and evaporated. The residue was separated by silica gel column chromatography using an EtOAc (ethyl acetate)/petroleum ether mixture (ratio 70/30) to give compound 2, a diol, as a white solid. 1.29 g (3.21 mmol) of the solid diol was extracted for a 64% isolated yield. The reaction is shown below in A:

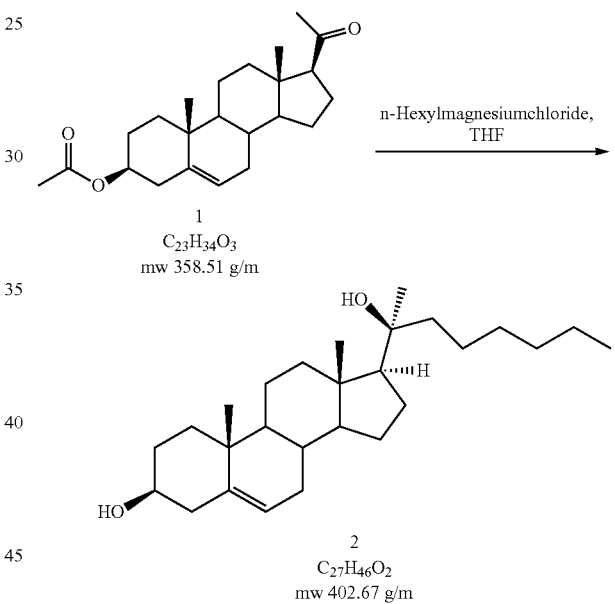

Figure 6:
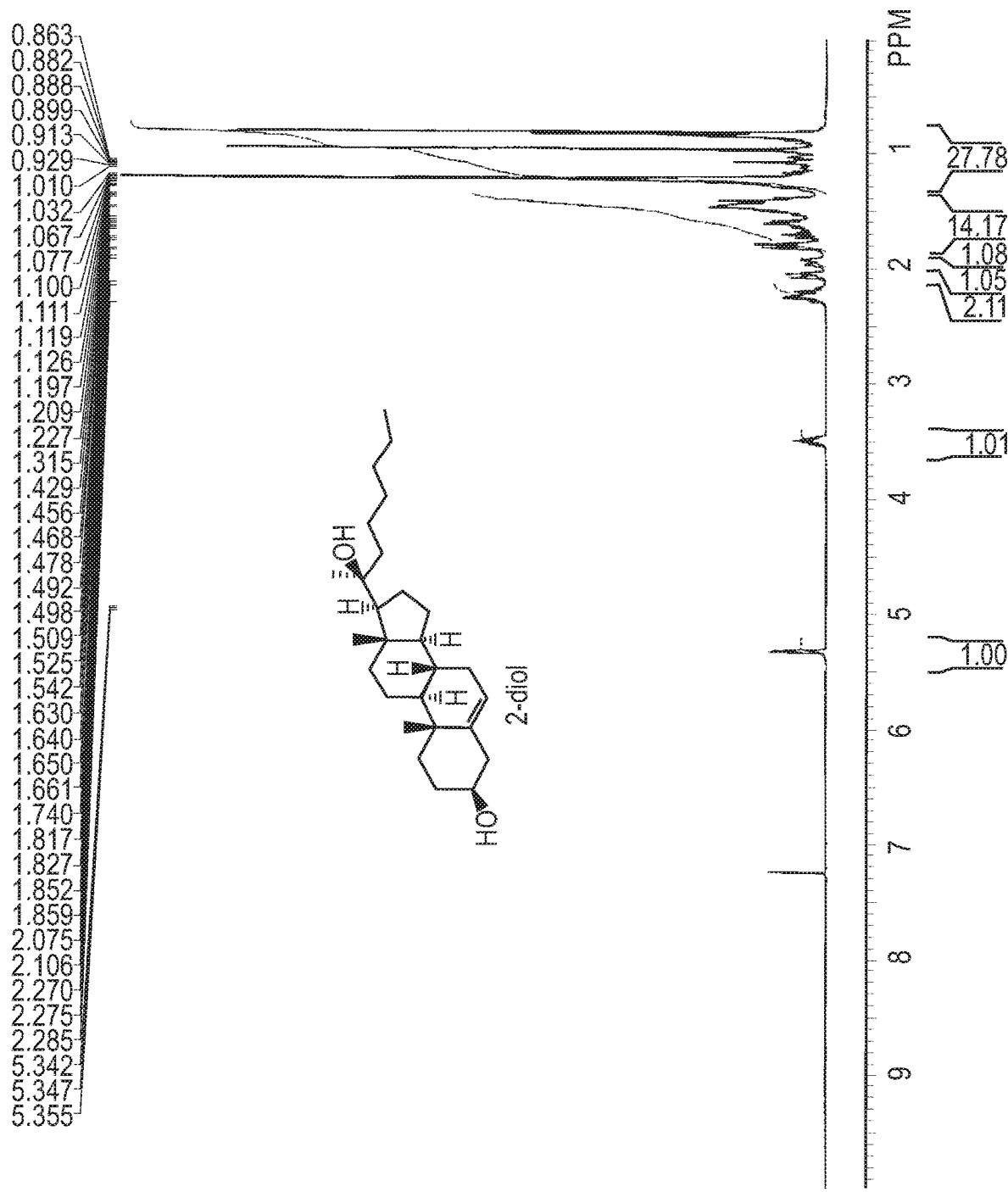
FIG. 6 is a graphic illustration of $^1$H NMR data obtained from the intermediary sterol or diol to synthesize Oxy133.
Figure 7:
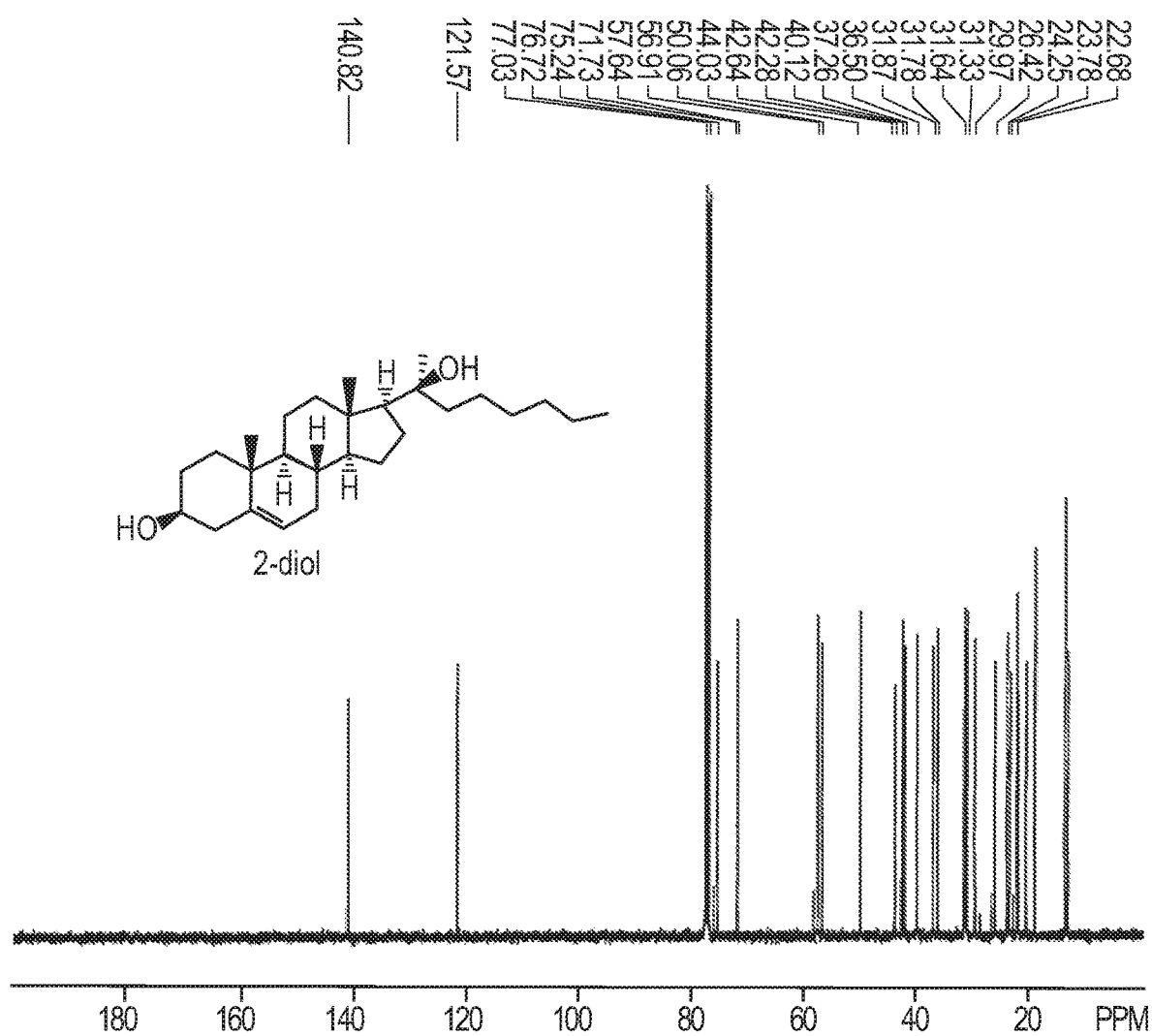
FIG. 7 is a graphic illustration of $^{13}$C NMR data obtained from the intermediary sterol or diol to synthesize Oxy133.

The $^1H$ NMR data of the diol in $CDCl_3$ at 400 MHz illustrated the following: δ: 0.8-1.9 (40H), 1.98 (m, 1H), 2.09 (m, 1H), 2.23 (m, 1H), 2.29 (m, 1H), 3.52 (m, 1H), 5.35 (m, 1H) in FIG. 6. The $^{13}C$ NMR data of the diol in $CDCl_3$ at 100 MHz in FIG. 7 illustrated the following: d: 13.6, 14.1, 19.4, 20.9, 22.4, 22.6, 23.8, 24.2, 26.4, 30.0, 31.3, 31.6, 31.8, 31.9, 36.5, 37.3, 40.1, 42.3, 42.6, 44.0, 50.1, 56.9, 57.6, 71.7, 75.2, 121.6, 140.8.

The diol created has an IUPAC name of (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 2

Preparation from Pregnenolone

Alternatively to Example 1, compound 2 of reaction scheme A above can be prepared from pregnenolone shown below in B utilizing the same procedure as utilized for the conversion of compound 1 to compound 2. In this procedure 10 g of pregnenolone was converted to 7.05 g of compound 2, which accounted for a 55% yield.

Reaction Scheme B

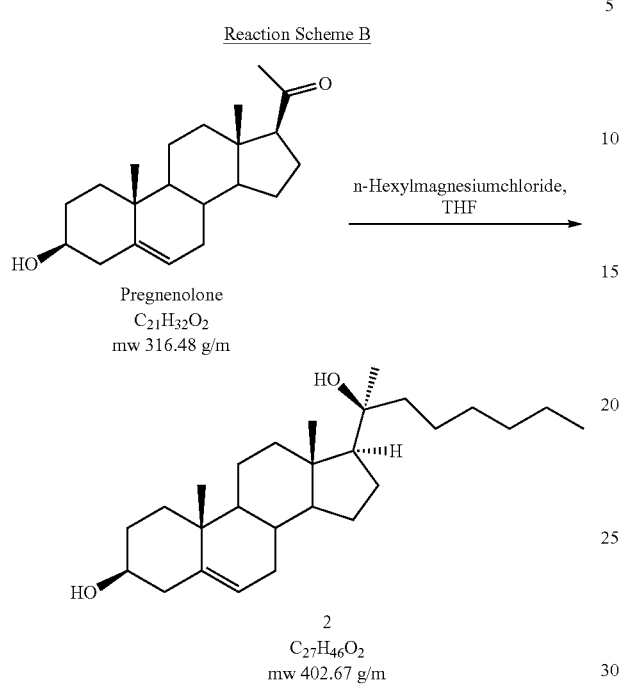

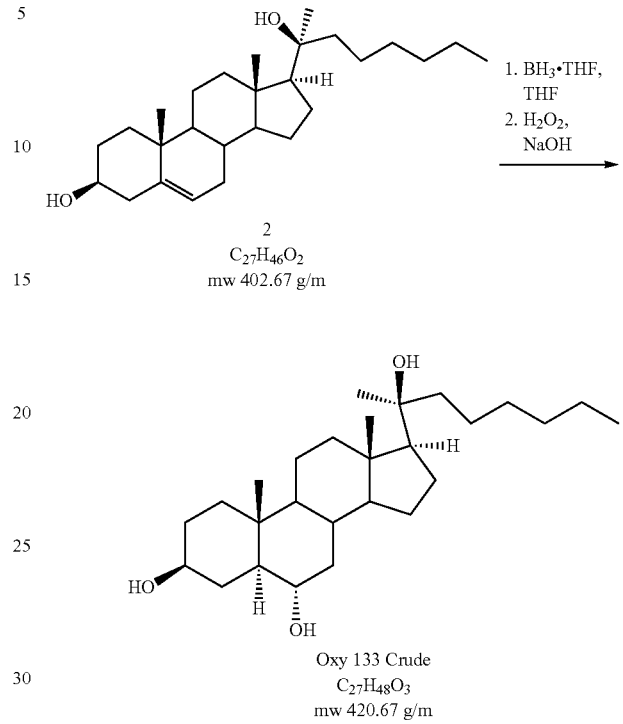

2500 mL of n-hexylmagnesium chloride (2 M, 5 mol) was charged to a reactor and the solution was cooled to −5° C. A solution of pregnenolone acetate in THF was charged to the reactor at a rate which maintained the internal reaction temperature below 1° C. The pregnenolone solution contained 500 g pregnenolone (1.4 mol) in 8 liters THF. After the addition was complete, the mixture was held at 0° C. for 1 hour then allowed to warm to room temperature overnight. The reaction mixture had become a solid, gelatinous mass. 2 liters of additional THF was added followed by 10 ml of glacial acetic acid. The reaction mixture was cooled to 5° C. and quenched by the addition of 350 ml of glacial acetic acid which gave a solution. The reaction mixture was concentrated under reduced pressure to a thick syrup. The compound was dissolved in dichloromethane, washed with water and finally washed with saturated sodium bicarbonate. The organic layer was concentrated under reduced pressure to an amber oil. Mass recovery was about 800 grams. The crude material was utilized as is in the next step.

The diol created has an IUPAC name of (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 3

The crude hexyl diol product (800 grams) was dissolved in 8 liters of THF, charged to a reactor, and was cooled to −5° C. 6300 mL of borane-THF complex (1 M, 6.3 moles, 4.5 equivalents) in THF was charged at a rate which maintained the internal reaction temperature below 1° C. Once the addition was complete, the reaction mixture was stirred at 0° C. for 1.5 hours then allowed to warm to room temperature overnight. The reaction is shown below.

The reaction mixture was quenched by addition of a mixture of 10% sodium hydroxide (4750 mL) and 30% hydrogen peroxide (1375 mL). The quench was extremely exothermic and required several hours to complete. The internal temperature was maintained below 10° C. After the addition of the quench volume was complete, the mixture was held cold for 1.5 hours then allowed to warm to room temperature overnight. 8 liters of dichloromethane was then added. The organic layer was isolated and washed with 7 liters of fresh water, and was concentrated under reduced pressure. The product was isolated as a viscous, oily mass which solidified on standing.

The product was dissolved in 4 liters of dichloromethane and was placed onto a silica gel column prepared in dichloromethane. The column was eluted first with 25% ethyl acetate to elute the 7-methyl-7-tridecyl alcohol by-product. Subsequently, the column was eluted with 10% methanol-ethyl acetate to solvate the Oxy133. The collected fractions were combined and concentrated under reduced pressure to a waxy solid. The compound was dissolved in acetone-water mixture (3:1) and concentrated under reduced pressure to remove residual solvents. The resulting crude Oxy133 was utilized in the next step.

Alternatively, the viscous product recovered from the hydroboration/oxidation can be solidified by stirring with heptanes, and the product isolated by filtration. The isolated product is suspended in methylene chloride (7.3 mL methylene chloride/g solid). The product was isolated by filtration and used as-is in the next step.

Example 4

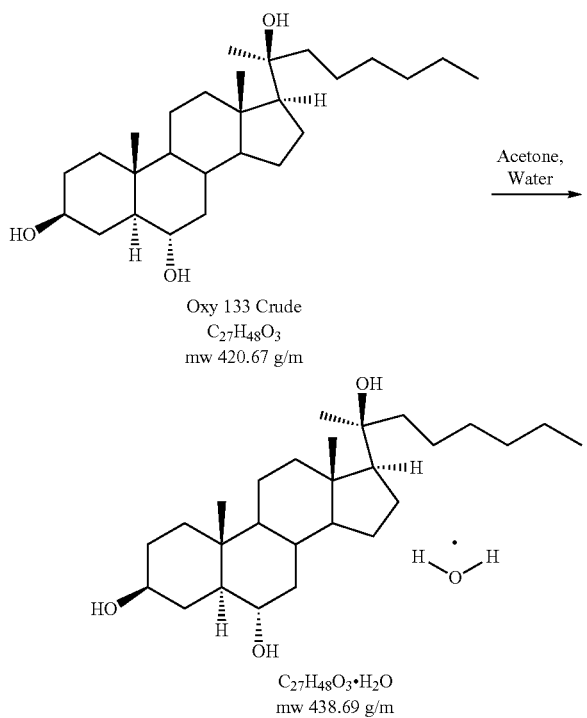

Oxy133 was recrystallized by dissolving 630 grams of crude oxy133 into 1500 ml of a 3:1 acetone/water mixture at reflux, then cooling to room temperature. The crystalline solid was recovered by vacuum filtration and dried to afford 336 g, which was a 28% overall yield from compound 1. The Oxy133 produced was monohydrous, and has an IUPAC name of (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol, monohydrate.

The $^1$H NMR data of Oxy133 in CDCl$_3$ at 400 MHz illustrated the following: δ: 0.66 (m, 1H), 0.85 (m, 10H), 1.23 (m, 18H), 1.47 (m, 9H), 1.68 (m, 4H), 1.81 (m, 1H), 1.99 (m, 1H), 2.06 (m. 1H), 2.18 (m, 1H), 3.42 (m, 1H), 3.58 (m, 1H). The $^{13}$C NMR data of Oxy133 in CDCl$_3$ at 400 MHz illustrated the following: d: 13.7, 14.0, 14.3, 21.2, 22.5, 22.8, 23.9, 24.4, 26.6, 30.1, 31.1, 32.1, 32.5, 33.9, 36.5, 37.5, 40.4, 41.7, 43.1, 44.3, 51.9, 53.9, 56.5, 57.9, 69.6, 71.3, 75.4. The infrared spectroscopy data of Oxy133 showed peaks at 3342 cm$^{-1}$, 2929 cm$^{-1}$, 2872 cm$^{-1}$, 2849 cm$^{-1}$. The turbo spray mass spectrometry data of the Oxy133 showed peaks at 438.4 m/z [M+NH$_4$]+, 420.4 m/z [M-H$_2$O+NH$_4$]+, 403.4 m/z [M-H$_2$O+H]+, 385.4 m/z [M-2H$_2$O+H]+. The $^1$H NMR, $^{13}$C NMR, IR, and MS of Oxy133 data are shown in FIGS. 2, 3, 4 and 5, respectively.

Example 5

Alternative One-Vessel Procedure from Pregnenolone Acetate 100 mL n-hexylmagnesium chloride (2M in THF, 200 mmol) was charged to a flask and cooled to −10° C. A solution containing 20 g pregnenolone acetate (56 mmol) in 200 ml of anhydrous THF was added dropwise, while maintaining the internal reaction temperature below −10° C. After the addition was completed, the mixture was stirred for 30 minutes then allowed to warm to room temperature. After 4 hours at room temperature, the mixture had become a gelatinous stirrable mass. The mixture was cooled to 0° C. and 200 mL Borane-THF complex (1M in THF, 200 mmol) was added dropwise, while maintaining the internal temperature below 0° C. Once addition was complete, the resulting solution was allowed to warm to room temperature overnight.

The mixture was cooled to 0° C. and quenched by the slow addition of a mixture of 10% NaOH (190 mL) and 30% H$_2$O$_2$ (55 mL). Once the quench was complete, the mixture was extracted with MTBE (800 mL total) resulting in an emulsion. Brine was added and the layers were separated. The organic phase was concentrated under reduced pressure to a clear, viscous oil. The oil was further purified utilizing the plug column method previously described.

In the following examples, sample analyses of OXY133 or OXY133 monohydrate as an API in different early phase batches were analyzed by HPLC followed by CAD in an assay method for the determination of OXY133 and OXY133 related impurities.

Example 6—HPLC Parameters and CAD Settings

A suitable HPLC system with a CAD detector, autosampler, column heater, and data acquisition system useful for the method of this disclosure included Agilent 1100 HPLC with ESA Corona plus Charged Aerosol Detector (CAD) using Empower 3 software for analysis. In some embodiments, the column used was Waters XBridge Phenyl, 4.6 mm×150 mm, 3.5 µm. An equivalent column could be used provided system suitability criteria are met. Other standard laboratory equipment included an analytical balance capable of weighing to 0.01 mg, laboratory class A glassware including volumetric flasks and pipets and HPLC screw cap vials.

In some aspects, reagents and standards suitable for the assay method of this disclosure included Oxy133 reference standard of known purity; Impurity 1 related compound standard; diol related compound standard; acetonitrile (ACN), HPLC grade or equivalent; tetrahydrofuran (THF), HPLC grade or equivalent; methanol (MeOH), HPLC grade or equivalent; and water, high purity, ≥18 megaΩ, suitable for use with HPLC, e.g. milli-Q water. Equivalent materials could be used as long as system suitability requirements are met. The settings for HPLC/CAD system and the gradient program used in these examples are summarized in Tables 2 and 3 above.

Example 7—Preparation of Mobile Phases and Method Diluent

In this example, solutions of Mobile Phase A, Mobile Phase B and a Method Diluent as required for the assay method of this disclosure were prepared. Formic acid was not required for the CAD analysis of Mobile Phase A and Mobile Phase B. However, if LC-MS is required for identification or peak purity analysis 1% formic acid (HPLC grade or equivalent) should be added to each mobile phase.

Mobile Phase A was prepared by filling a glass reservoir of 100% Milli-Q water to an appropriate volume to cover the entire analysis. This preparation was suitable for use when stored under ambient conditions for up to one week after preparation. Mobile Phase B was prepared in a glass reservoir with 100% methanol HPLC grade or better. This solution was suitable for up to three months stored at ambient conditions.

A Method Diluent of acetonitrile:tetrahydrofuran, 1:1, volume by volume, was prepared by combining equal volumes of acetonitrile and tetrahydrofuran in a suitable glass container to meet the requirements of the standard and sample preparations and was mixed well. This solution was suitable for up to one month when stored at ambient conditions. All reference and sample solutions were prepared in the Method Diluent.

In the following examples Standard Solutions of a Reference Standard Solution, an OXY133 Quantitation Level Solution, an Impurity 1 Standard Solution and a Diol Standard Solution were prepared.

Example 8—Preparation of OXY133 Quantitation Level (QL) Solution

First an Oxy133 Reference Standard Solution (500 µg/mL) was prepared by weighing 25±0.5 mg of Oxy133 Reference Standard. The resulting solution was transferred to a 50-mL volumetric flask, where it was dissolved, diluted to volume with the Method Diluent prepared above and sonicated briefly to complete dissolution. The approximate concentration of Oxy133 Reference Standard was 500 µg/mL. (Solution ID: RS500)

For the preparation of Oxy133 QL Solution (0.5 µg/mL), an OXY133 Intermediate QL solution was first prepared by diluting the 500 µg/mL Reference Standard using the Method Diluent to obtain a 5 µg/mL solution. This was accomplished by pipetting 1 mL of the Oxy133 Reference Standard Solution into a 100-mL volumetric flask, which was brought to volume with the Method Diluent, and mixed to complete dissolution. (Solution ID: QL5) 5 µg/mL Intermediate QL (QL5) solution was diluted using the Method Diluent to result in the 0.5 µg/mL solution of Oxy133 as the QL solution. In particular, 1.0 mL of the Oxy133 Reference Standard Solution and 9.0 mL of Method Diluent were mixed into a glass culture tube with PTFE lined cap thereby forming the Oxy133 QL Solution. (Solution ID: OQL0.5)

Example 9—Preparation of Impurity 1 Standard Solution

Impurity 1 Standard Solution (0.5 µg/mL) was prepared by weighing 5±0.1 mg of Impurity 1 Reference Standard was weighed into a glass vessel and pipetting 20.0 mL of Method Diluent into the same vessel; the resulting mixture was mixed to complete dissolution. The approximate concentration of the Impurity1 Stock Standard was 250 µg/mL. (Solution ID: Imp250)

250 µg/mL Impurity 1 Stock Standard Solution was diluted using the Method Diluent to result in 0.5 µg/mL Impurity 1 QL solution. 0.050 mL of the Imp250 solution was delivered using preferably a Hamilton syringe or a positive displacement pipet into a 25 mL volumetric flask containing about 10 mL of Method Diluent. The resulting mixture was brought to volume with Method Diluent and mixed. (Solution ID: IQL0.5).

Example 10—Preparation of Diol Standard Solution

For the preparation of Diol Standard Solution (0.5 µg/mL), 5±0.1 mg of Diol Reference Standard was weighed into a glass vessel, 20.0 mL of Method Diluent was pipetted into the same vessel, and the resulting mixture was then mixed to complete dissolution. The approximate concentration of the Diol Stock Standard was 250 µg/mL. (Solution ID: Diol250) 250 µg/mL Diol Stock Standard Solution was diluted using the Method Diluent to result in the 0.5 µg/mL Diol QL solution. 0.050 mL of the Diol250 solution was delivered using preferably a Hamilton syringe or a positive displacement pipet into a 25 mL volumetric flask containing about 10 mL of Method Diluent. The resulting mixture was brought to volume with the Method Diluent and mixed. (Solution ID: DQL0.5)

Example 11—Preparation of a Drug Substance Formulation Sample

Drug Substance Formulation Samples were prepared by accurately weighing an appropriate amount of drug substance into a volumetric flask to result in a concentration equivalent to the Oxy133 Reference Standard concentration. Method Diluent was then added to approximately half of the volume of the volumetric flask. Brief sonication was used to solubilize the drug substance and Method Diluent was added in sufficient quantity and mixed. A portion of the solution was transferred into a HPLC vial for analysis. The amount of API in this sample can be described on a weight-per-volume basis. Sample concentration were calculated as shown below:

$$\text{Sample } Conc. \text{ (µg/mL)} = \frac{\text{Standard } Conc. \text{ (µg/mL)} \times \text{Sample Area}}{\text{Mean Area of six Precision Standard Injections}}$$

This calculation can be used only for Oxy133 which is the API. The related compounds can be reported as area percent compared to the Oxy133 and/or mg/mL in each sample injection.

Example 12—Suitability of a HPLC/CAD System for the Analysis of OXY133

The system suitability testing was successfully carried out prior to the analysis of OXY133 samples according to the protocol described below.

A minimum of at least two Diluent Blank injections were run to ensure a stable baseline, wherein the second Diluent Blank was free from interference in the region of the Oxy133 peak. Significant interference was defined as any peak with a signal-to-noise (s/n) ratio of ≥10, at the retention time of the Oxy133 peak.

Six reference standard injections were subsequently run. The relative standard deviation or coefficient of variation (% RSD, or CV) for the peak areas of the six replicate injections of the Reference Standard Solution was ≤2.0%.

Thereafter, three quantitation level (QL) Standard Solutions of OXY133 QL, Impurity 1 QL and Diol QL as prepared in Examples 8-10 were run. These were followed by runs of one Bracketing Reference Standard, six sample solutions of a drug substance containing OXY133 and a final Bracketing Reference Standard. These runs are summarized below in Table 5 as follows:

TABLE 5

Sequence of Injections

| Vial Contents | Number of Injections |
|---|---|
| Diluent Blank | At least 2 |
| Reference Standard | 6 |
| 3 QL Solution(s) (OQL0.5 + IQL0.5 + DQL0.5) | 1 each |
| Bracketing Reference Standard | 1 |
| Sample Solution(s) | 6 samples |
| Bracketing Reference Standard | 1 |

The U.S. Pharmacopeia (USP) resolution observed for Oxy133 in the reference and bracketing standards, was ≥0.8 for the D1 diastereomer. The QL injection had a visible peak with a USP s/n value ≥10. Bracketing Reference Standard areas were within ±2% of the mean of the six Reference Standard Solutions injected at the start of the run. For QL injections of Impurity 1 and Diol: each injection showed a visible peak for each compound at the 0.5 µg/mL concentration free from interference in the region of the analyte OXY133 peak.

The HPLC/CAD System precision was demonstrated throughout these runs by injecting a Reference Standard after at least every six sample injections. These standards were identified as Bracketing Reference Standards (BRS). Additionally, each run was ended with a BRS injection.

The concentration of the above standard, reference and sample of OXY133 solutions were calculated as follows:

Oxy133 Standard Concentration Calculation (mg/mL)

$$Oxy133\,(mg/mL) = \frac{Oxy133\text{ Weight in mg} \times Purity}{Final\ Volume\ (mL)}$$

Where: Purity = Purity of Oxy133 Standard

Bracketing Reference Standard Calculation $$\%\ Agreement = \frac{Area\ of\ BRS \times 100}{Mean\ Area\ of\ Six\ WS\ injections}$$

Oxy133 Sample Concentration Calculation (µg/mL)

$$Oxy133\,(\mu g/mL) = \frac{STC\,(\mu g/mL) \times SA}{ST}$$

where:
SA=Sample Peak Area
ST=Mean peak area of six Reference Standard injections
STC=Standard Concentration (µg/mL)
Area Percent Calculation for Impurities (Not Impurity 1 nor Diol)

$$Area\ Percent = \frac{Impurity\ Peak\ Area \times 100}{Total\ Peaks\ Area}$$

Where:
Impurity Peak Area=Area of impurity peak
Total Peaks Area=Sum of areas of all peaks present
100=Conversion to percent.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for determining purity in a sample of OXY133, the method comprising:
   providing an HPLC eluent comprising OXY133, OXY133 impurities and a mobile volatile phase;
   generating an aerosol of liquid droplets from the HPLC eluent;
   drying the droplets to obtain residue particles of OXY133;
   contacting the OXY133 residue particles with an ion stream which applies a size-dependent electrical charge to each of the residue particles to generate an electrical signal having a level proportional to the amount of charged residue particles of OXY133; and measuring the electrical signal to determine the purity of OXY133 in the sample, wherein OXY133 comprises OXY133 monohydrate or OXY133 dihydrate.

2. A method of claim 1, further comprising transferring the charged residue particles of OXY133 to a collector and measuring the electrical signal with an electrometer.

3. A method of claim 1, wherein OXY133 monohydrate impurities comprise OXY133 impurity 1, a $C_{27}H_{46}O_2$ diol, diastereomer D1 and diastereomer D2 of OXY133 monohydrate.

4. A method of claim 2, wherein generating the aerosol of liquid droplets from the HPLC eluent is provided by a nebulizer.

5. A method of claim 1, wherein the mobile volatile phase comprises acetonitrile, a mixture of acetonitrile and water, a mixture of water and methanol or a mixture of water, methanol and acetonitrile.

6. A method of claim 3, wherein OXY133 monohydrate impurities are detected from about 0.03% to about 0.05%.

7. A method of claim 3, wherein a resolution of the OXY133 peak and the D1 diastereomer is ≥0.8.

8. A method of claim 1, wherein the OXY133 monohydrate is detected in an amount of about 0.01% or 1 ng.

9. A method of claim 1, wherein OXY133 monohydrate is separated from diastereomer D1, diastereomer D2 or other OXY133 monohydrate impurity.

10. A method of claim 1, wherein the purity of OXY133 monohydrate is at least 96.9%.

11. A method for determining the amount of OXY133 in a sample, the method comprising:
    providing an OXY133 reference standard having a known quantity of OXY133 measurable by HPLC-CAD;
    providing the sample having an unknown quantity of OXY133;
    separating the amount of OXY133 in the sample by HPLC-CAD; and
    the amount of OXY133 in the sample.

12. A method of claim 11, wherein the reference standard comprises at least 500 µg/mL of OXY133 monohydrate.

13. A method of claim 11, wherein the sample is prepared in a solution of acetonitrile:tetrahydrofuran, 1:1, volume by volume.

14. A method of claim 11, wherein the sample comprises a mobile phase from the HPLC-CAD, which comprises water or methanol.

15. A method of claim 11, wherein OXY133 comprises diastereomer D1, diastereomer D2, $C_{27}H_{46}O_2$ diol or OXY133 monohydrate impurity 1.

16. A method of claim 15, wherein diastereomer D1 of OXY133 is detected at a resolution of ≥0.8.

17. A method of claim 11, wherein the retention time of OXY133 is 14.04 minutes, of diastereomer D1 is 13.6 minutes and of diastereomer D2 is 14.6 minutes.

18. A method for determining purity in a sample of OXY133, the method comprising:

reacting a diol having the formula:

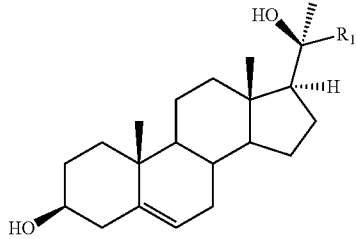

with borane, hydrogen peroxide and tetrahydrofuran to form an oxysterol or a pharmaceutically acceptable salt, hydrate or solvate thereof having the formula:

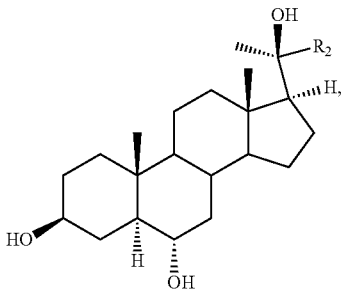

wherein R1 and R2 comprise a hexyl group and the diol comprises (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol (OXY133);

subjecting the OXY133 to HPLC to obtain an eluent comprising OXY133, impurities of OXY133 and a volatile mobile phase; and charging the HPLC eluent into a CAD detector to determine the purity of OXY133.

19. A method according to claim 1, wherein OXY133 is recovered and placed in a pharmaceutical formulation.

* * * * *